(12) United States Patent
Cao et al.

(10) Patent No.: US 9,364,162 B2
(45) Date of Patent: Jun. 14, 2016

(54) REJECTING OVERSENSING DUE TO NOISE

(75) Inventors: Jian Cao, Shoreview, MN (US); Jeffrey M. Gillberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 1163 days.

(21) Appl. No.: 12/772,578

(22) Filed: May 3, 2010

(65) Prior Publication Data

US 2011/0196247 A1   Aug. 11, 2011

Related U.S. Application Data

(60) Provisional application No. 61/303,572, filed on Feb. 11, 2010.

(51) Int. Cl.
| | | |
|---|---|---|
| *A61N 1/37* | (2006.01) | |
| *A61B 5/00* | (2006.01) | |
| *A61B 5/0464* | (2006.01) | |
| *A61N 1/362* | (2006.01) | |

(52) U.S. Cl.
CPC .............. *A61B 5/0464* (2013.01); *A61B 5/7203* (2013.01); *A61B 5/7207* (2013.01); *A61B 5/7217* (2013.01); *A61N 1/37* (2013.01); *A61N 1/3622* (2013.01); *A61N 1/3718* (2013.01)

(58) Field of Classification Search
USPC ........................................................ 600/509
See application file for complete search history.

(56) References Cited

U.S. PATENT DOCUMENTS

| | | | |
|---|---|---|---|
| 4,374,382 A | 2/1983 | Markowitz | |
| 5,117,824 A | 6/1992 | Keimel et al. | |
| 5,545,186 A | 8/1996 | Olson et al. | |
| 5,755,736 A | 5/1998 | Gillberg et al. | |
| 5,776,168 A | 7/1998 | Gunderson | |
| 6,236,882 B1 * | 5/2001 | Lee et al. | 600/509 |
| 6,321,115 B1 * | 11/2001 | Mouchawar et al. | 607/9 |
| 6,505,071 B1 * | 1/2003 | Zhu et al. | 607/28 |
| 7,027,858 B2 * | 4/2006 | Cao et al. | 600/521 |
| 7,047,083 B2 | 5/2006 | Gunderson et al. | |
| 7,236,828 B2 | 6/2007 | Casavant et al. | |
| 7,289,851 B2 | 10/2007 | Gunderson et al. | |
| 7,333,855 B2 | 2/2008 | Gunderson et al. | |
| 7,369,893 B2 | 5/2008 | Gunderson | |
| 7,539,540 B2 | 5/2009 | Gunderson et al. | |
| 7,567,835 B2 | 7/2009 | Gunderson et al. | |
| 2007/0232948 A1 * | 10/2007 | Stadler et al. | 600/512 |
| 2008/0082012 A1 * | 4/2008 | Gunderson et al. | 600/509 |
| 2008/0082014 A1 | 4/2008 | Cao et al. | |

FOREIGN PATENT DOCUMENTS

WO    2005018738 A1    3/2005

OTHER PUBLICATIONS

International Search Report and Written Opinion from corresponding PCT Application Serial No. PCT/US2010/033376 dated Sep. 27, 2010 (10 pages).
Reply to Written Opinion from corresponding PCT Application Serial No. PCT/US2010/033376 filed Feb. 14, 2011 (10 pages).
International Preliminary Report on Patentability from corresponding PCT Application Serial No. PCT/US2010/033376 dated Jan. 30, 2012 (13 pages).

* cited by examiner

*Primary Examiner* — William Levicky

(57) ABSTRACT

In general, this disclosure is directed to signal processing based methods to reject oversensing due to electromagnetic interference or other noise without compromising tachyarrhythmia detection sensitivity. A method comprises sensing a signal indicative of cardiac activity, detecting a cardiac event based on the signal, determining a count of fluctuations of the signal within a window between the detected cardiac event and a next cardiac event, and determining whether noise is present in the signal based on the count.

26 Claims, 20 Drawing Sheets

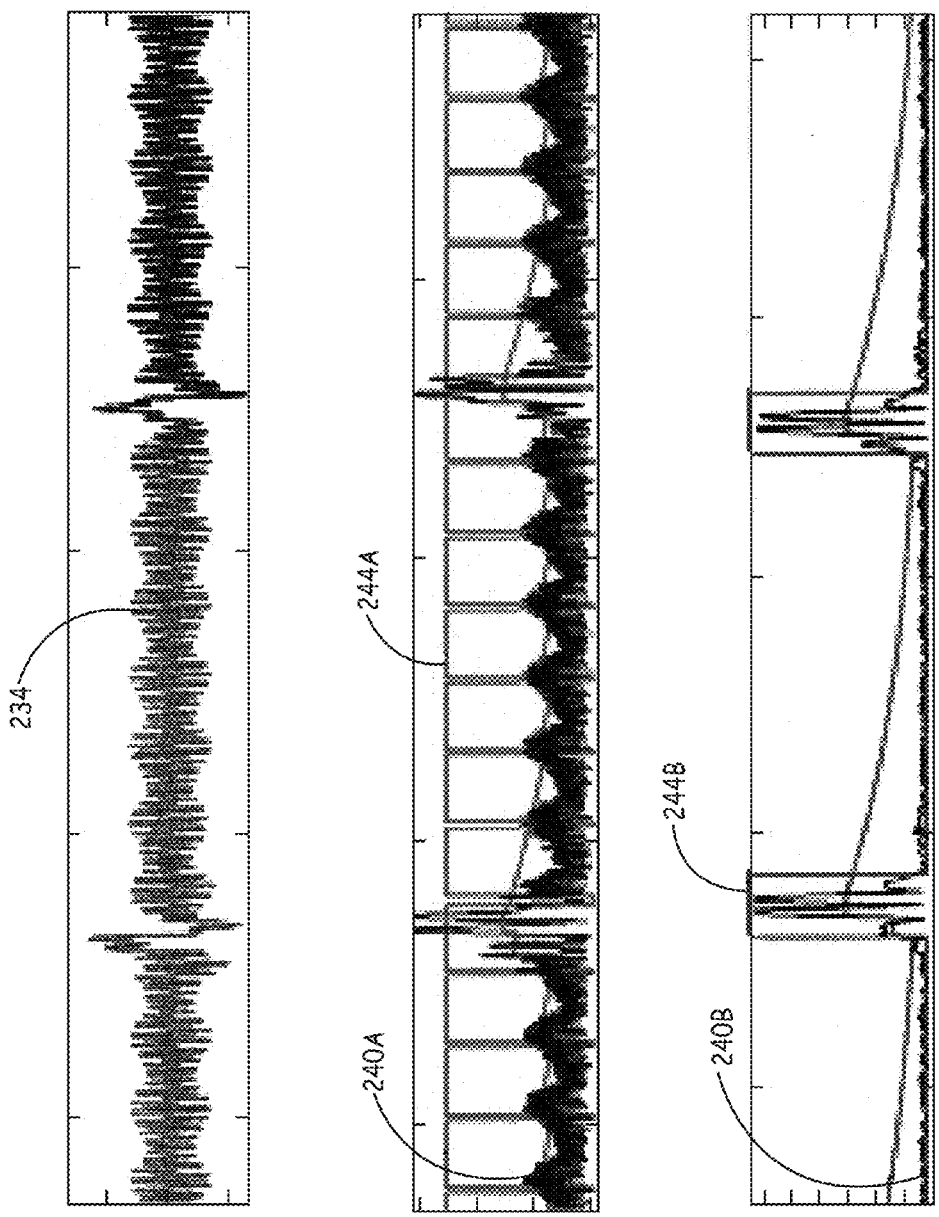

REJECTING OVERSENSING DUE TO NOISE

This application claims the benefit of U.S. Provisional Application No. 61/303,572, entitled "REJECTING OVERSENSING DUE TO NOISE," and filed on Feb. 11, 2010, the entire content of which is incorporated herein by reference.

TECHNICAL FIELD

The invention relates to medical devices, and, more particularly, to medical devices that sense a signal indicative of cardiac activity.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscle, nerve, brain, stomach or other organs or tissues. Some therapies include the delivery of electrical signals, e.g., stimulation, to such organs or tissues. Some medical devices may employ one or more elongated electrical leads carrying electrodes for the delivery of therapeutic electrical signals to such organs or tissues, electrodes for sensing intrinsic electrical signals within the patient, which may be generated by such organs or tissue, and/or other sensors for sensing physiological parameters of a patient.

Medical leads may be configured to allow electrodes or other sensors to be positioned at desired locations for delivery of therapeutic electrical signals or sensing. For example, electrodes or sensors may be carried at a distal portion of a lead. A proximal portion of the lead may be coupled to a medical device housing, which may contain circuitry, such as signal generation and/or sensing circuitry. In some cases, the medical leads and the medical device housing are implantable within the patient. Medical devices with a housing configured for implantation within the patient may be referred to as implantable medical devices.

Implantable cardiac pacemakers or cardioverter-defibrillators, for example, provide therapeutic electrical signals to the heart via electrodes carried by one or more implantable medical leads. The therapeutic electrical signals may include pulses or shocks for pacing, cardioversion, or defibrillation. In some cases, a medical device may sense intrinsic depolarizations of the heart, and control delivery of therapeutic signals to the heart based on the sensed depolarizations. Upon detection of an abnormal rhythm, such as bradycardia, tachycardia or fibrillation, an appropriate therapeutic electrical signal or signals may be delivered to restore or maintain a more normal rhythm. For example, in some cases, an implantable medical device may deliver pacing stimulation to the heart of the patient upon detecting bradycardia or tachycardia, and deliver cardioversion or defibrillation shocks to the heart upon detecting tachycardia or fibrillation.

If noise, such as noise due to electromagnetic interference (EMI), is present on a signal used to sense depolarizations of the heart, a medical device may incorrectly detect abnormal cardiac rhythms. More particularly, rapid signal fluctuations due to EMI or other noise may be interpreted by a medical device as a plurality of sensed cardiac depolarizations, and result in the medical device inappropriately detecting a cardiac arrhythmia. The rate of sensed events when noise is present may be similar to or greater than that for detection of a tachyarrhythmia, and the medical device may detect a tachyarrhythmia based on the noise.

SUMMARY

In general, the disclosure describes techniques for reducing oversensing due to electromagnetic interference (EMI), e.g., due to contact with ungrounded electrical appliances, or other noise. EMI or other noise may result in false detection of atrial or ventricular tachyarrhythmias, e.g., ventricular tachycardia (VT) or ventricular fibrillation (VF), and subsequent unnecessary delivery of therapeutic electrical signals, e.g., pulses or shocks for pacing, cardioversion, or defibrillation. The signal processing techniques of this disclosure may reduce oversensing due to EMI or other noise without compromising tachyarrhythmia detection sensitivity.

In one example, a method comprises sensing a signal indicative of cardiac activity, detecting a cardiac event based on the signal, determining a count of fluctuations of the signal within a window between the detected cardiac event and a next cardiac event, and determining whether noise is present in the signal based on the count.

In another example, a system comprises a sensor that senses a signal indicative of cardiac activity, a sensing module that detects a cardiac event based on the signal, and determines a count of fluctuations of the signal within a window between the detected cardiac event and a next cardiac event, and a processor that determines whether noise is present in the signal based on the count.

In another example, a system comprises means for sensing a signal indicative of cardiac activity, means for detecting a cardiac event based on the signal, means for determining a count of fluctuations of the signal within a window between the detected cardiac event and a next cardiac event, and means for determining whether noise is present in the signal based on the count.

In another example, a computer readable medium comprises instructions. The instructions cause a programmable processor to receive a signal indicative of cardiac activity, detect a cardiac event based on the signal, determine a count of fluctuations of the signal within a window between the detected cardiac event and a next cardiac event, and determine whether noise is present in the signal based on the count.

The details of one or more examples are set forth in the accompanying drawings and the description below. Other features, objects, and advantages will be apparent from the description and drawings, and from the claims.

BRIEF DESCRIPTION OF DRAWINGS

FIG. 19 illustrates an example EGM in which a notch filter is applied to attenuate 60 Hz noise.

DETAILED DESCRIPTION

Oversensing may cause painful inappropriate shocks in patients with implantable cardioverter defibrillators (ICDs). For example, episodes of electromagnetic interference (EMI) may cause false detections of ventricular fibrillation (VF) and result in subsequent unnecessary delivery of shocks or other therapeutic electrical signals to patients with ICDs. Current ICDs may not reject EMI signals due to the need of high sensitivity for tachyarrhythmia sensing and detection. In general, this disclosure is directed to signal processing based methods to reject oversensing due to EMI or other noise without compromising tachyarrhythmia detection sensitivity.

Although the noise detection techniques of this disclosure are primarily described herein with respect to detecting EMI, these techniques may be utilized to detect other types of noise. For example, the noise detection techniques of this disclosure my detect noise due to muscle or other motion artifacts, lead fractures or disconnections, magnetic resonance imaging, and other non-physiological noise. Furthermore, although described herein primarily with reference to detection of noise in ventricular electrograms to avoid inappropriate detection of ventricular tachyarrhythmia, e.g., ventricular tachycardia (VT) or VF, the techniques described herein may additionally or alternatively be applied for detection of noise in atrial electrograms to avoid inappropriate detection of atrial tachyarrhythmia, e.g., atrial tachycardia, fibrillation, or flutter, or for detection of noise in surface electrocardiograms.

Figure 1:
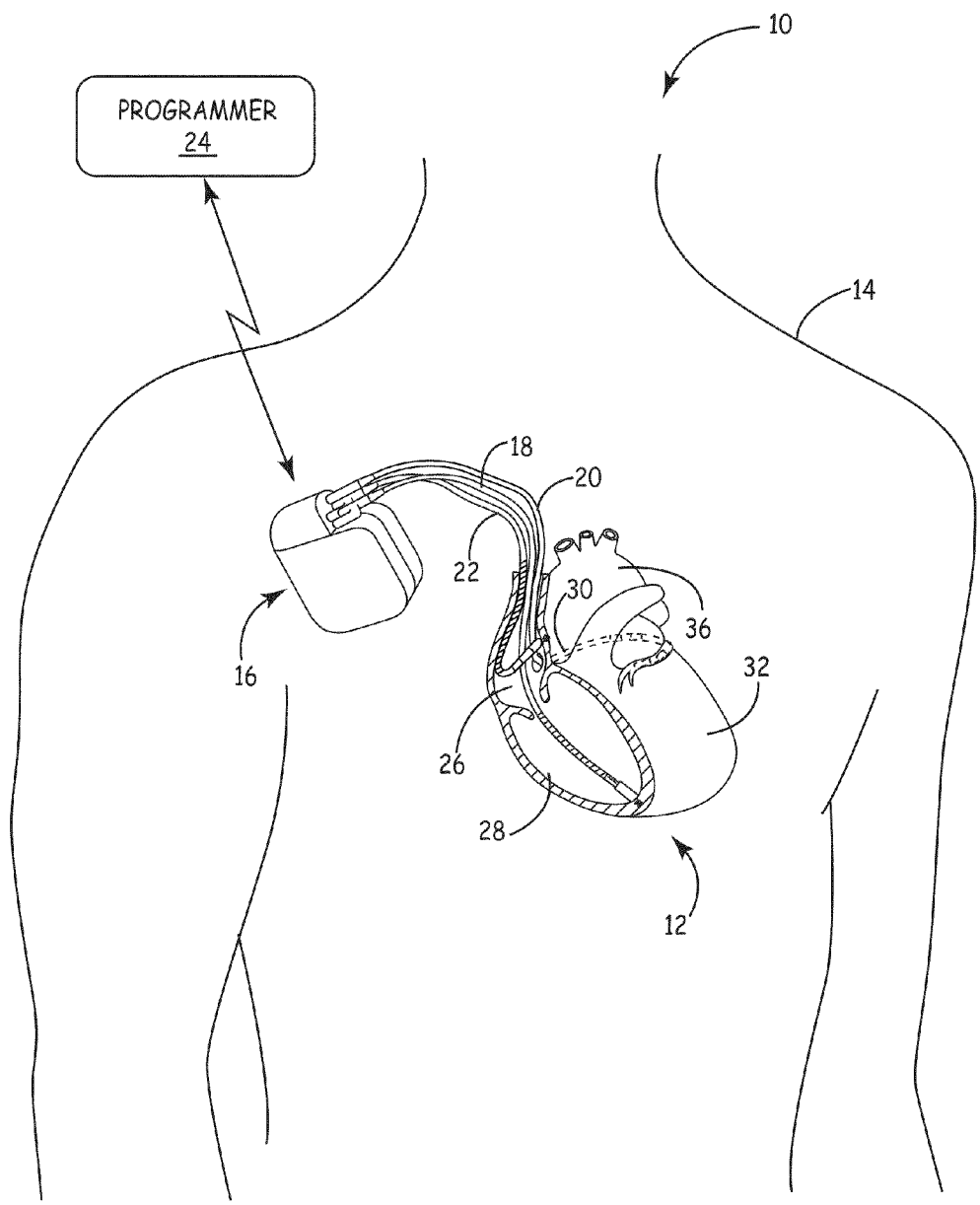
FIG. 1 is a conceptual drawing illustrating an example system that includes an implantable medical device (IMD) coupled to implantable medical leads.

FIG. 1 is a conceptual diagram illustrating an example system 10 that may be used for sensing of physiological parameters of patient 14 and/or to provide therapy to heart 12 of patient 14. System 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily a human patient.

Although an implantable medical device and delivery of electrical stimulation to heart 12 are described herein as examples, the techniques for reducing oversensing due to noise of this disclosure may be applicable to other medical devices and/or other therapies. In general, the techniques described in this disclosure may be implemented by any medical device, e.g., implantable or external, that senses a signal indicative of cardiac activity, or any one or more components of a system including such a medical device. As one alternative example, IMD 16 may be a cardiac monitor that monitors a rhythm of heart 12, such as a Reveal® XT/DX implantable cardiac monitor, commercially available from Medtronic Inc. of Minneapolis, Minn.

In the example of FIG. 1, leads 18, 20, 22 extend into the heart 12 of patient 16 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, system 10 may additionally or alternatively include one or more leads or lead segments (not shown in FIG. 1) that deploy one or more electrodes within the vena cava or other vein. These electrodes may allow alternative electrical sensing configurations that may provide improved or supplemental sensing in some patients. Furthermore, in some examples, system 10 may additionally or alternatively include temporary or permanent epicardial or subcutaneous leads, instead of or in addition to transvenous, intracardiac leads 18, 20 and 22. Such leads may be used for one or more of cardiac sensing, pacing, or cardioversion/defibrillation.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of the atria 26 and 36 and/or ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art.

In some examples, programmer 24 comprises a handheld computing device, computer workstation, or networked computing device. Programmer 24 may include a user interface that receives input from a user. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, and 22, or a power source of IMD 16. In some examples, this information may be presented to the user as an alert. For example, noise detection according to the techniques described herein may trigger IMD 16 to transmit an alert to the user via programmer 24.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2A:
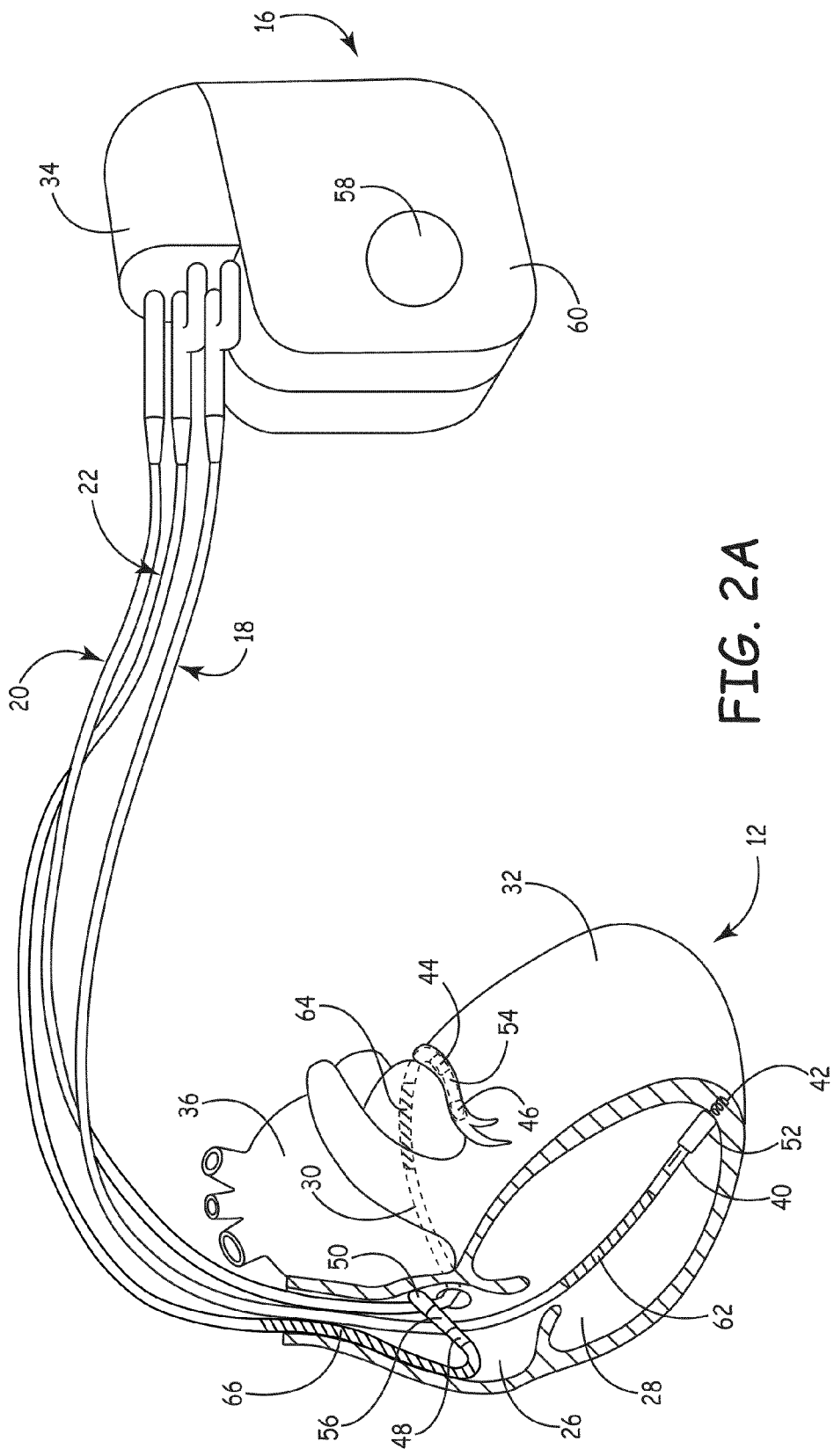
FIG. 2A is a conceptual drawing illustrating the example IMD and leads of FIG. 1 in conjunction with a heart.

FIG. 2A is a conceptual diagram illustrating IMD 16 and leads 18, 20 and 22 of system 10 in greater detail. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2A, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The combination of electrodes used for sensing may be referred to as a sensing configuration.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes. The combination of electrodes used for delivery of stimulation or sensing, their associated conductors and connectors, and any tissue or fluid between the electrodes, may define an electrical path.

The configuration of system 10 illustrated in FIGS. 1 and 2A is merely one example. In other examples, a system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

Figure 2B:
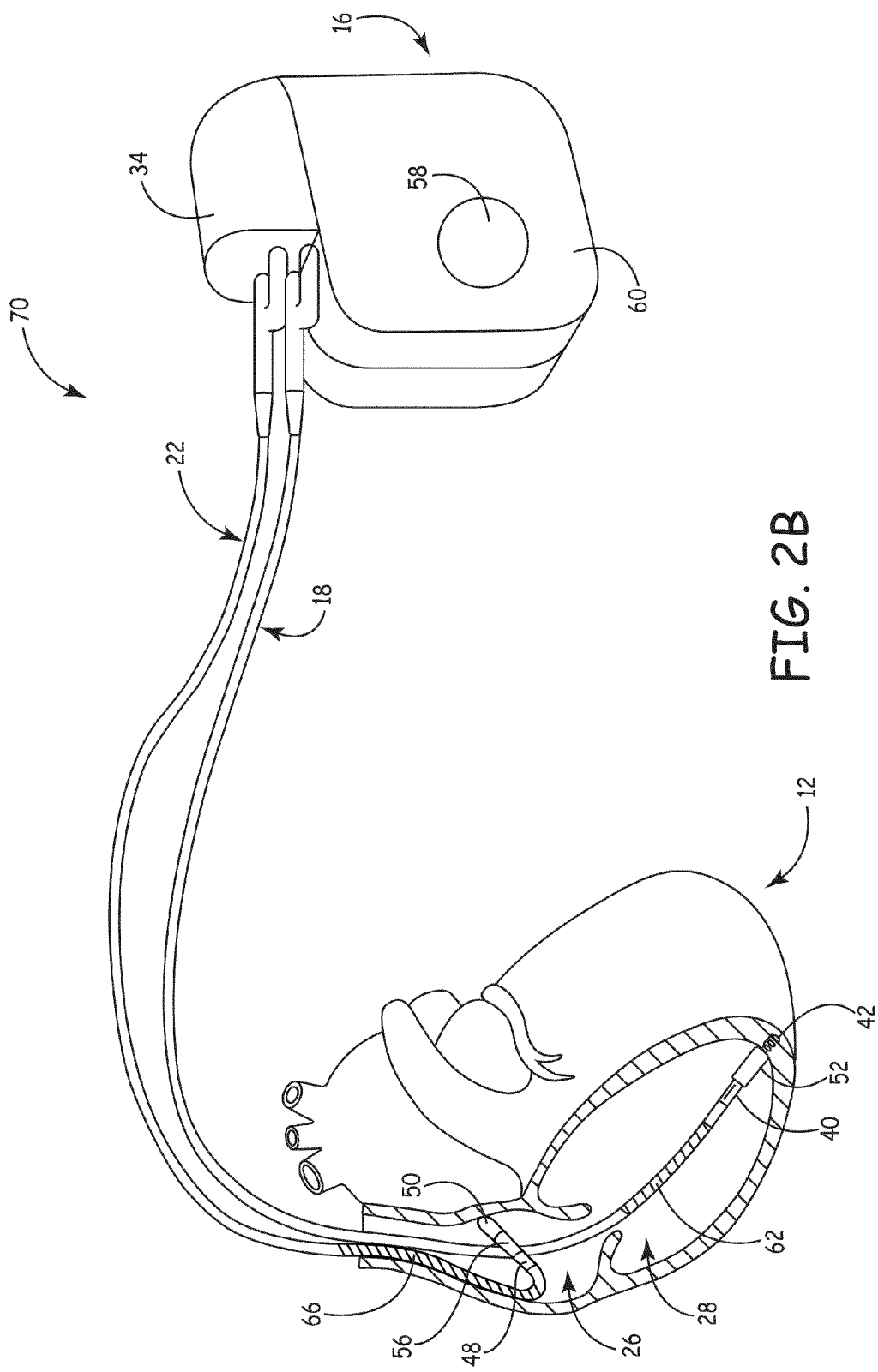
FIG. 2B is a conceptual drawing illustrating the example IMD of FIG. 1 coupled to a different configuration of implantable medical leads in conjunction with a heart.

In addition, in other examples, a system may include any suitable number of leads coupled to IMD 16, and each of the leads may extend to any location within or proximate to heart 12. For example, other examples of systems may include three transvenous leads located as illustrated in FIGS. 1 and 2, and an additional lead located within or proximate to left atrium 36. As another example, other examples of systems may include a single lead that extends from IMD 16 into right atrium 26 or right ventricle 28, or two leads that extend into a respective one of the right ventricle 26 and right atrium 26. An example of this type of system is shown in FIG. 2B. Any electrodes located on these additional leads may be used in sensing and/or stimulation configurations.

FIG. 2B is a conceptual diagram illustrating another example system 70, which is similar to system 10 of FIGS. 1 and 2, but includes two leads 18, 22, rather than three leads. Leads 18, 22 are implanted within right ventricle 28 and right atrium 26, respectively. System 70 shown in FIG. 2B may be useful for physiological sensing and/or providing pacing, cardioversion, or other therapies to heart 12. Detection of noise according to this disclosure may be performed in two lead systems in the manner described herein with respect to three lead systems.

Figure 3:
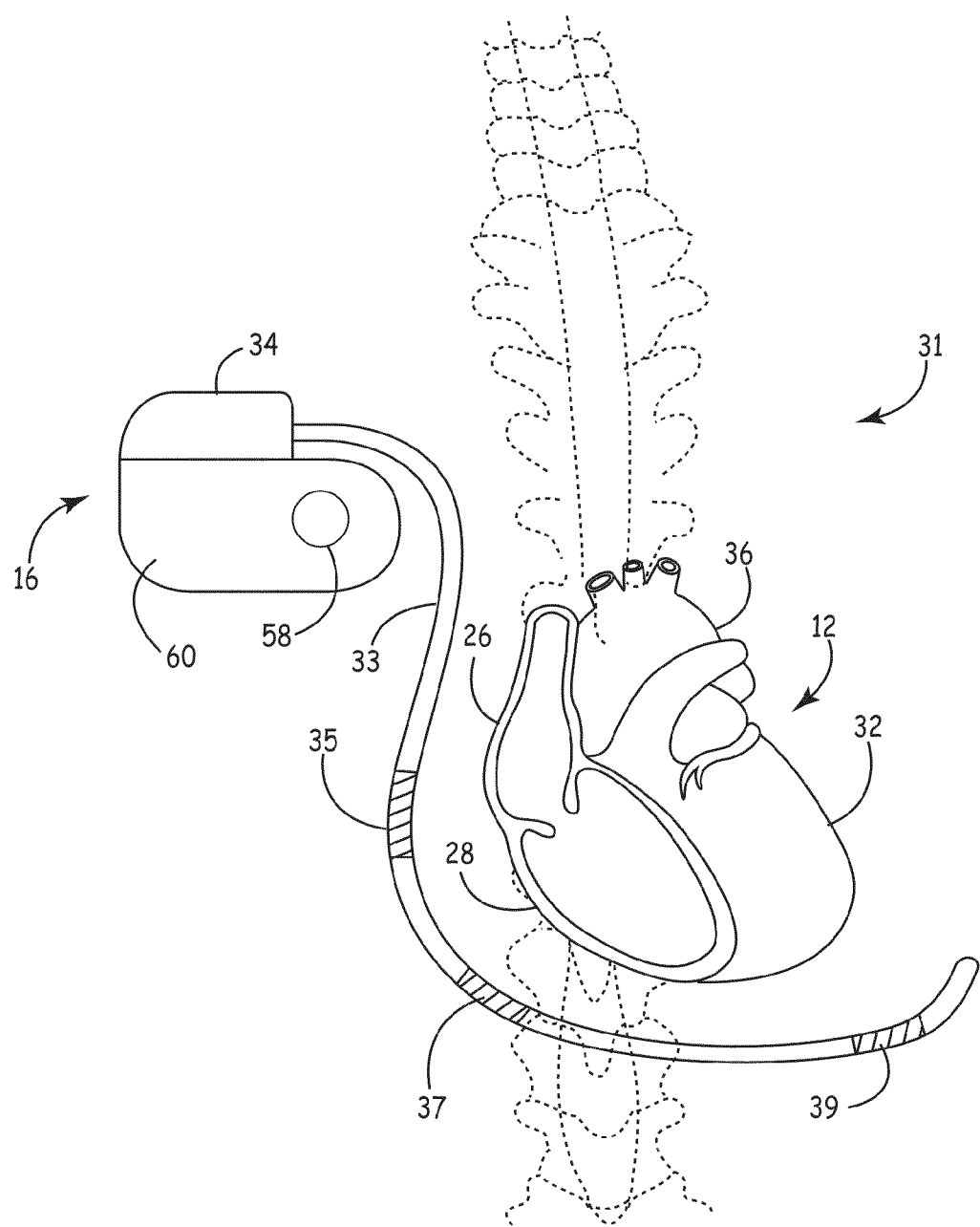
FIG. 3 is a conceptual diagram illustrating an example subcutaneous system that includes an IMD coupled to an implantable medical lead.

FIG. 3 is a conceptual diagram illustrating an example subcutaneous system 31 that may be used for sensing of physiological parameters of patient 14 and/or to provide therapy to heart 12 of patient 14. Although the noise detection techniques of this disclosure are primarily described with respect to system 10, these techniques may utilized by other systems, such as system 31. System 31 includes IMD 16 and lead 33, which includes electrodes 35, 37, and 39. In the example illustrated in FIG. 3, lead 31 is positioned within patient 14 such that electrodes 35, 37, and 39 are proximate to heart 12. In this way, IMD 16 may deliver electrical stimulation therapy to heart 12 via at least electrodes 35, 37, and 39 of lead 33. As described with respect to FIG. 2A, IMD 16 may include one or more housing electrodes, such as housing electrode 58, which may also deliver electrical stimulation therapy to heart 12.

In the example illustrated in FIG. 3, electrodes 35, 37, and 39 are implanted proximate to, but outside of heart 12. Therefore, electrodes 35, 37, and 39 may be referred to as extravascular electrodes. An extravascular electrode may comprise an electrode that is not implanted within heart 12 or within an artery or other vasculature of the patient 14. For example, electrodes 35, 37, and 39 may comprise subcutaneous, submuscular, epicardial, and/or intramural electrodes.

IMD 16 may deliver pacing pulses via any combination of electrodes 35, 37, 39 and housing electrode 58, e.g., any unipolar or bipolar electrode configuration, to cause depolarization of cardiac tissue of heart 12. IMD 16 may alternatively or additionally deliver defibrillation and/or cardioversion pulses to heart 12 via electrodes 35, 37, 39, and 58. Electrodes 35, 37, and 39 may comprise elongated electrodes that take the form of coil electrodes. Such coil electrodes may be useful in delivering high energy defibrillation pulses to heart 12.

The number, configuration, and type of electrodes 35, 37, 39, and 58 shown in FIG. 3 are merely exemplary. In other examples, lead 33 may include any number, configuration, and type of electrodes 35, 37, and, 39. For example, lead 33 may include one or more additional electrodes proximate to heart 12, e.g., proximate to left atrium 36. In the example illustrated in FIG. 3, system 31 includes a single lead 33. In other examples, system 31 may include two or more leads.

As another example, a system may include both electrodes positioned within heart 12, as illustrated in system 10, and electrodes positioned outside of heart 12, as illustrated in system 31. As another example, a system may not include any leads. Instead, a system may sense physiological parameters of patient 14 and/or to provide therapy to heart 12 of patient 14 via a plurality of housing electrodes. Housing electrodes, such as housing electrode 58, may, for example, be formed integrally with an outer surface of hermetically-sealed housing 60 of IMD 16 or otherwise coupled to housing 60.

Figure 4:
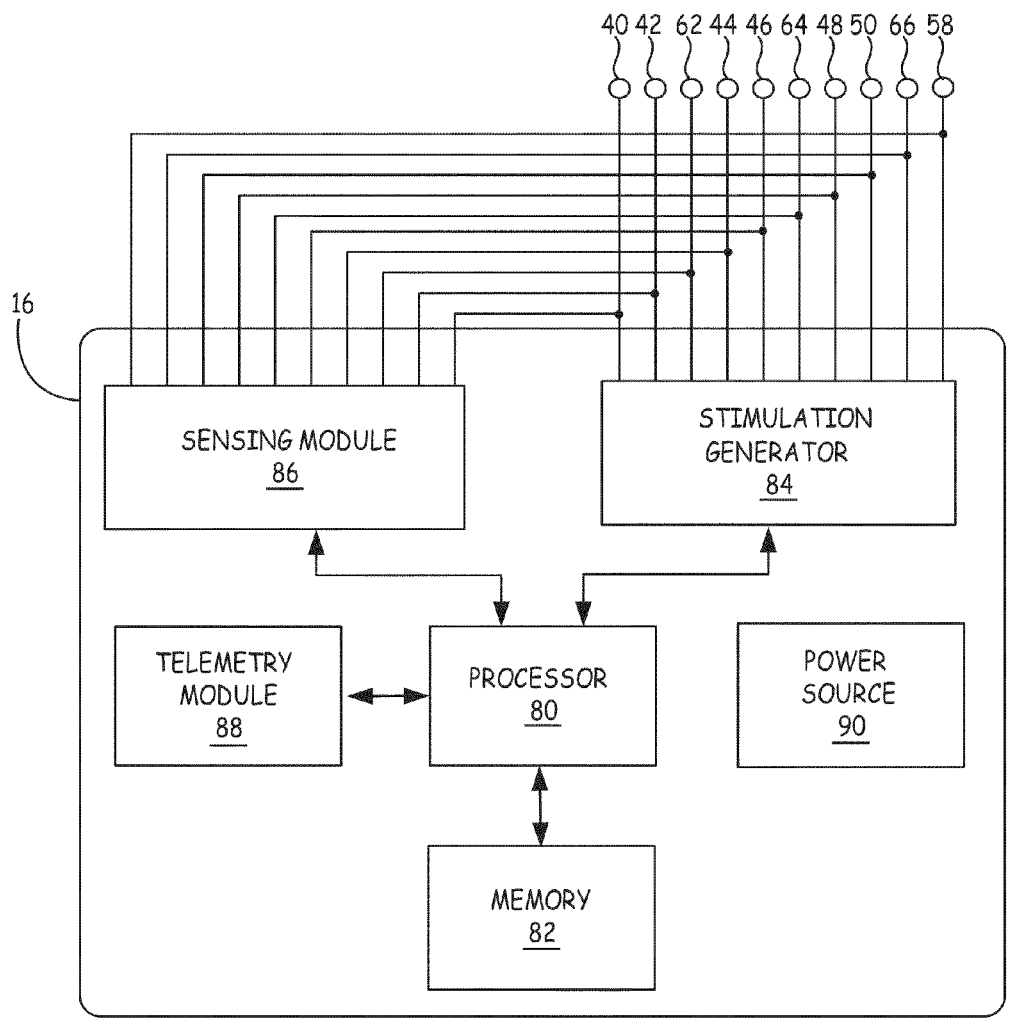
FIG. 4 is a functional block diagram illustrating an example configuration of the IMD of FIG. 1.

FIG. 4 is a functional block diagram illustrating an example configuration of IMD 16. In the illustrated example, IMD 16 includes a processor 80, memory 82, signal generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to a selected one or more of therapy programs, which may be stored in memory 82. For example, processor 80 may control stimulation generator 84 to deliver electrical pulses with the amplitudes, pulse widths, frequency, or electrode polarities specified by the selected one or more therapy programs.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12. Sensing module 86 may also include a switch module to select which of the available electrodes are used to sense the heart activity, depending upon which electrode combination is used in the current sensing configuration. In some examples, processor 80 may select the electrodes that function as sense electrodes, i.e., select the sensing configuration, via the switch module within sensing module 86. Sensing module 86 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 80, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 80 may control the functionality of sensing module 86 by providing signals via a data/address bus.

Processor 80 may include a timing and control module, which may be embodied as hardware, firmware, software, or any combination thereof. The timing and control module may comprise a dedicated hardware circuit, such as an ASIC, separate from other processor 80 components, such as a microprocessor, or a software module executed by a component of processor 80, which may be a microprocessor or ASIC. The timing and control module may implement programmable counters. If IMD 16 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR and other modes of pacing.

Intervals defined by the timing and control module within processor 80 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 86 for a time interval during and after delivery of electrical stimulation to heart 12. The durations of these intervals may be determined by processor 80 in response to stored data in memory 82. The timing and control module of processor 80 may also determine the amplitude of the cardiac pacing pulses.

Interval counters implemented by the timing and control module of processor 80 may be reset upon sensing of R-waves and P-waves with detection channels of sensing module 86. In examples in which IMD 16 provides pacing, signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. In such examples, processor 80 may reset the interval counters upon the generation of pacing pulses by signal generator 84, and thereby control the basic timing of cardiac pacing functions, including anti-tachyarrhythmia pacing.

The value of the count present in the interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as VF or VT. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects tachycardia when the interval length falls below 220 milliseconds (ms) and fibrillation when the interval length falls below 180 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by signal generator 84 may be loaded by processor 80 into the timing and control module to control the operation of the escape interval counters therein and to define refractory periods during which detection of R-waves and P-waves is ineffective to restart the escape interval counters for the an anti-tachyarrhythmia pacing. In the event that processor 80 detects an atrial or ventricular tachyarrhythmia based on signals from sensing module 86, and a cardioversion or defibrillation shock is desired, processor 80 may control the amplitude, form and timing of the shock delivered by signal generator 84.

As described in greater detail below, IMD 16, and more particularly processor 80, may be configured to detect noise in signals received by sensing module 86. In response to determining that noise, e.g., EMI, is present, processor 80 may take one or more actions. As one example, processor 80 may withhold detection of a tachyarrhythmia, such as VT or VF, for a user-defined time, e.g., approximately 5 seconds to approximately 10 seconds, subsequent to determining that noise is present. Additionally or alternatively, processor 80 may withhold delivery of one or more types of therapies intended to address tachyarrhythmia, e.g., withhold defibrillation. As another example, processor 80 may withhold tachyarrhythmia detection, e.g., of VF and/or VT, for one or more heartbeats, to reject EMI or other noise. As another example, a tachyarrhythmia counter, e.g., number of intervals to detect or NID counter, may be decremented if processor 80 detects noise for one or more heartbeats. In some examples, the counter may be decremented or not incremented for each beat for which noise is detected As another example, in response to detecting noise, processor 80 may withhold tachyarrhythmia detection if processor 80 determines noise is present for a specified percentage of sensed cardiac events, e.g., a specified percentage of sensed heartbeats. For example, processor 80 may withhold tachyarrhythmia detection if noise is detected for N (N=1, 2, 3, etc.) of M (M=10, 20, 30, etc.) sensed heartbeats. As described in further detail below, e.g., with respect to FIG. 18, processor 80 may detect noise based on a current heartbeat and one or more, e.g., two, preceding heartbeats. This moving window may allow processor 80 to withhold tachyarrhythmia detection during episodes of noise without delaying detection of true tachyarrhythmias.

In examples in which ICD 16 delivers pacing signals to heart 12 of patient 14, processor 80 may switch pacing modes subsequent to detecting noise. For example, processor 80 may implement a noise reversion ventricular pacing mode that delivers asynchronous pacing to one or more ventricles at a fixed pacing rate. Noise reversion pacing may not be based on sensed cardiac events, such as sensed atrial depolarizations. Instead, noise reversion pacing may be delivered at a fixed rate that is independent of sensed cardiac events. The noise reversion pacing mode may be implemented for a defined time period or until processor 80 no longer detects the presence of noise.

As another example, processor 80 may activate a supplemental filter to filter the signals received by sensing module 86 subsequent to determining noise is present. In some examples, supplemental filter 122 is activated for a defined time period, e.g., of approximately 5 seconds to approximately 3 minutes. As one example, supplemental filter 122 is activated for approximately 45 seconds. As another example, processor 80 may continue to monitor the non-filtered signal to determine when noise is no longer present. Since supplemental filter 122 may pose some risk of filtering out cardiac events, supplemental filter may only be activated when processor 80 determines that noise is present.

In some examples, processor 80 may provide an alert to a user, e.g., of programmer 24, regarding any detected noise condition via telemetry module 88. Additionally or alternatively, processor 80 may suggest a response to a noise condition and/or receive user approval of a response via telemetry module 88. Alternatively, processor may provide an electrogram (EGM) or other sensed signal to an external device, e.g., programmer 24, via telemetry module 88 for further evaluation of noise conditions.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals, e.g., EGMs, produced by atrial and ventricular sense amplifier circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In addition, processor 80 may transmit information regarding noise conditions to programmer 24 via telemetry module 88. For example, processor 80 may provide an alert regarding any detected noise conditions, suggest a response to a noise condition, or provide an EGM or other sensed signal for further evaluation of noise conditions to programmer 24 via telemetry module 88. Processor 80 may also receive information regarding noise conditions or responses to such conditions from programmer 24 via telemetry module 88.

In some examples, IMD 16 may signal programmer 24 to further communicate with and pass the alert through a network such as the Medtronic CareLink® Network developed by Medtronic, Inc., of Minneapolis, Minn., or some other network linking patient 14 to a clinician.

Figure 5:
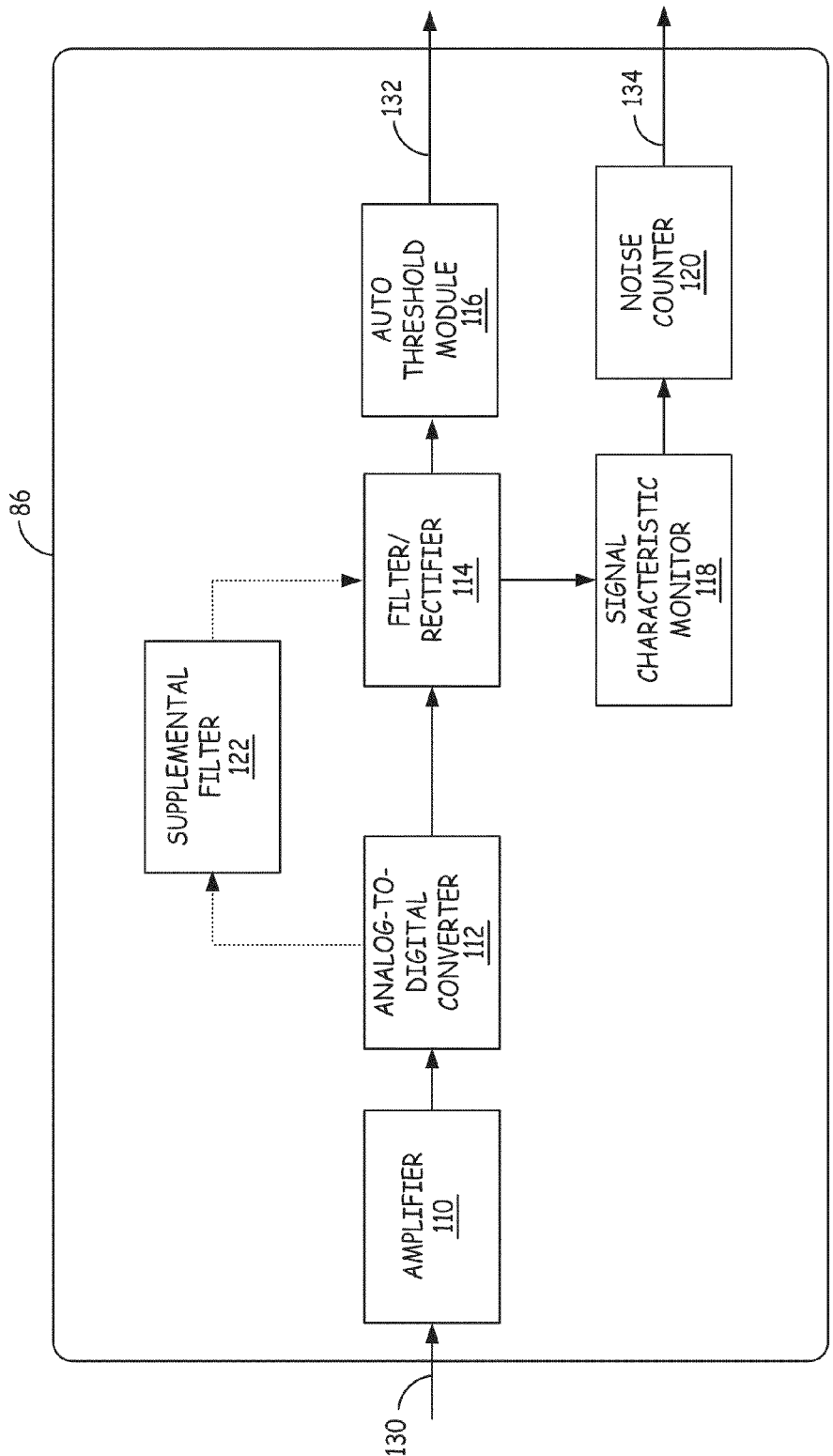
FIG. 5 is a functional block diagram illustrating an example configuration of a sensing module of the IMD of FIG. 1.

FIG. 5 is a functional block diagram illustrating an example configuration of sensing module 86 of IMD 16 of FIG. 4. In the illustrated example, sensing module 86 includes an amplifier 110, analog-to-digital (A/D) converter 112, filter/rectifier 114, auto threshold module 116, signal characteristic monitor 118, noise counter 120, and supplemental filter 122.

Some or all of the components of sensing module 86 may in other examples be implemented processor 80 (FIG. 4) of IMD 16. In some examples, signal characteristic monitor 118 and noise counter 120 are implemented in processor 80. The components of sensing module 86 may be implemented as hardware, software, or any combination thereof. In some examples, certain components of sensing module 86, such as amplifier 110, A/D converter 112, filter/rectifier 114, auto threshold module 116, and supplemental filter 122 are implemented as hardware, while others, such as signal characteristic monitor 118 and noise counter 120, are implemented as firmware, e.g., software within IMD 16. In other examples, all, or some subset of the components of sensing module 86, such as signal characteristic monitor 118 and noise counter 120, may be implemented in another device, such as an external programmer or other external computing device.

In some examples, sensing module 86 may include multiple channels, e.g., to process multiple signals simultaneously. For example, sensing module 86 may apply signal processing techniques for noise detection to multiple signals simultaneously. As one example, sensing module 86 may receive EGMs for multiple electrode sensing configurations, e.g., right ventricle (RV) tip to RV ring, RV tip to RV coil, RV coil to housing, left ventricle (LV) tip to LV ring, and/or LV tip to LV coil, simultaneously, and determine whether noise is present on each of the received EGM signals. Applying noise detection techniques to multiple EGMs may improve analysis of EGM morphology and help to further reduce inappropriate detection of tachyarrhythmias, e.g., VF and/or VT, and subsequent therapy, e.g., defibrillation shocks. In some example, sensing module 86 may simultaneously process other electrical signals for noise detection as well, e.g., one or more atrial EGMs, subcutaneous electrocardiograms (ECGs) and/or surface ECGs.

Amplifier 110 may receive a signal 130 indicative of cardiac activity, such as an electrogram (EGM), from one or more of electrodes 40, 42, 44, 46, 48, 50, 58, 62, 64 or 66, amplify the signal, and provide the amplified signal to A/D converter 112. In some examples, amplifier 110 may be an automatic gain controlled amplifier. A/D converter 112 may convert the amplified signal from an analog signal to a digital signal. Filter/rectifier 114 may receive the digitalized signal from A/D converter 112 and filter and rectify the digital signal.

In some examples, filter/rectifier 114 utilizes a bandpass filter. The range of frequencies that filter/rectifier 114 passes may be based on the type of cardiac event, e.g., P- or R-wave, that sensing module 86 and, more particularly, the selected detection channel of sensing module 86, is configured to detect. In particular, filter/rectifier 114 may pass frequencies that correlate with a selected type of cardiac event, e.g., P- or R-wave, and the amplitude of the filtered and rectified signal may vary according to how the signal amplitude in the frequency range that correlates with the selected type of cardiac event varies. As one example, filter/rectifier 114 may pass frequencies within the range of approximately 13 Hertz (Hz) to approximately 39 Hz when the selected detection channel of sensing module 86 is configured to detect R-waves.

Auto threshold module 116 may determine a threshold signal based on the filtered and rectified signal. The value of the threshold signal may automatically adjust based on the amplitude of the filtered and rectified signal. As previously described, the amplitude of the filtered and rectified signal may vary according to how the signal amplitude in the frequency range that correlates with a selected type of cardiac event, e.g., P- or R-wave, varies. In this manner, auto threshold module 116 may provide an adjustable sensing threshold as a function of the measured P- or R-wave amplitude of the heart rhythm.

Auto threshold module 116 may also compare values of the digital signal outputted by A/D converter 112 to values of the threshold signal and detect cardiac events, such as P waves and/or R-waves, based on the comparison. Auto threshold module 116 may provide indications 132 of detected cardiac events, such as P- and R-waves, to processor 80.

Signal characteristic monitor 118 may monitor a characteristic of the filtered and rectified signal output by filter/rectifier 114 to help facilitate noise recognition. In general, signal characteristic monitor 118 may provide an indication of the amplitude of the filtered and rectified signal, and noise counter 120 may increment based on fluctuations in the signal amplitude. Rapid signal fluctuations due to EMI or other noise may be interpreted by sensing module 86 as a plurality of sensed cardiac events, e.g., P- or R-waves, and result in inappropriate detection of a cardiac arrhythmia by IMD 16. More particularly, auto threshold module 116 of a sensing channel of sensing module 86 may interpret noise as cardiac events, e.g., P- or R-waves, and provide indications of the events 132 to processor 80. The rate of sensed events when noise is present may be similar to or greater than that for detection of a tachyarrhythmia, and processor 80 may detect a tachyarrhythmia based on the noise.

In one example, signal characteristic monitor 118 calculates a moving average of the filtered and rectified signal to help facilitate noise recognition. For example, signal characteristic monitor 118 may sample the filtered and rectified signal at approximately 1024 Hz and compute a moving average based on approximately 16 data points. Signal characteristic monitor 118 may also determine when a rising (or falling) edge of the filtered and rectified signal crosses a threshold value, e.g., approximately one half of the moving average, and increment noise counter 120 each time this occurs. In this manner, noise counter 120 may provide an indication of the number of signal fluctuations that may be attributed to noise, such as EMI. Signal characteristic monitor 118 may also require the value of the filtered and rectified signal to exceed a lower limit, such as one-fourth of a sensitivity setting, in order to increment noise counter 120. This may help prevent noise counter 120 from counting very low amplitude noise or non-noise signal fluctuations.

In other examples, signal characteristic monitor 118 may detect peaks of the filtered and rectified signal and increment noise counter 120 based on the peak detection. Signal characteristic monitor 118 may also monitor the amplitude of the detected peaks to ensure that only signal peaks that exceed a threshold value increment noise counter 120. In other examples, signal characteristic monitor 118 may low pass filter the filtered and rectified signal output by filter/rectifier 114 to determine a threshold for noise recognition. Signal characteristic monitor 118 may compare the filtered and rectified signal to the threshold determined based on low pass filtering to increment noise counter 120.

Signal characteristic monitor 118 may monitor a characteristic of the filtered and rectified signal within a sensing window to help facilitate noise recognition. For example, processor 80 may activate signal characteristic monitor 118 for a period of time corresponding to a sensing window upon auto threshold module 116 detecting a specified type of cardiac event, e.g., a P- or R-wave. The sensing window may correspond to a blanking period.

The blanking period may follow a detected cardiac event, e.g., a P- or R-wave. IMD 16 may withhold detection of cardiac events and therapy delivery during the blanking period. Therefore, noise detected during the blanking period may be due to sources other than therapy delivery. Furthermore, the sensing window, e.g., blanking period, may be sufficiently short such that signal fluctuations would not be physiologic, e.g., due to a subsequent normal or tachyarrhythmic cardiac depolarization, and instead would more likely be due to noise. For example, the sensing window may expire prior to a subsequent cardiac depolarization, e.g., a next cardiac event. Processor 80 may activate signal characteristic monitor 118 for a sensing window subsequent to each sensed cardiac event of a specified type, e.g., subsequent to each R-wave. As one example, the sensing window may be less than or equal to approximately 120 milliseconds (ms).

Processor 80 may determine whether noise is present based on the count 134 received from noise counter 120 upon expiration of a sensing window. For example, processor 80 may determine whether noise is present based on the noise count obtained during one sensing window associated with one heartbeat. If the count within noise counter 120 is greater than or equal to a threshold, e.g., is greater than or equal to approximately 10 counts, processor 80 may determine that noise, e.g., EMI, is present.

In some examples, processor 80 may determine whether noise is present based on a cumulative count obtained over a plurality of consecutive sensing windows. For example, processor 80 may determine that noise is present if the cumulative count over two consecutive heartbeats, e.g., R-waves, is greater than or equal to approximately 14 counts, and the interval between the two consecutive heartbeats, e.g., R-R interval, is less than 160 ms. As another example, processor 80 may determine that noise is present if the cumulative count over three consecutive heartbeats, e.g., R-waves, is greater than or equal to approximately 19 counts, and the interval from the first heartbeat to the third heartbeat is less than approximately 380 ms.

The various noise count rules, e.g., for one, two, and three heartbeats, may account for various types of high frequency noise. The most common EMI signals on EGMs are at frequencies of approximately 50 Hz and approximately 60 Hz. The noise count gathered for one heartbeat may be sufficient to detect this type of noise. Processor 80 may detect intermittent noise or other types of noise by monitoring the noise count over a plurality of heartbeats. The count within noise counter 120 may be reset to zero upon expiration of a sensing window. Processor 80 may store, e.g., with memory 82, noise count values for previous heartbeats. In general, tachyarrhythmias, e.g., VF, have high frequency signals, but the number of counts triggered for storage within noise counter 120 is less than the threshold set for noise detection. In this manner, sensing module 86 may detect high frequency noise, e.g., due to EMI, without falsely detecting noise due to tachyarrhythmias, such as VF.

In some examples, processor 80 may also determine that noise is present for a heartbeat if the filtered and rectified signal output by filter/rectifier 114 has an amplitude outside of a physiological range. For example, if the amplitude of the filtered and rectified signal exceeds a physiological threshold, e.g., 30 millivolts, processor 80 may determine that the signal is non-physiological and that noise is present for that heartbeat. In this manner, noise detection based on a physiological threshold may supplement noise detection based on the count of signal fluctuations.

Sensing module 86 may also include supplemental filter 122. Processor 80 may activate supplemental filter 122 upon determining that noise is present. In some examples, supplemental filter 122 may include one or more notch filters, e.g., that attenuate frequencies of approximately 50 Hz and/or approximately 60 Hz. As another example, supplemental filter 122 may be an adaptive noise reversion filter, e.g., that is adaptive to filter out the frequency of the detected noise. In other examples, supplemental filter 122 may be positioned elsewhere in sensing module 86, e.g., such that the number of counts triggered for storage within noise counter 120 is independent of whether supplemental filter 122 is ON or OFF.

Processor 80 may activate supplemental filter 122 to filter the digital signal output by A/D converter 112 subsequent to determining noise is present. In some examples, supplemental filter 122 is activated for a defined time period, e.g., of approximately 5 seconds to approximately 3 minutes. As one example, supplemental filter 122 is activated for approximately 45 seconds. As another example, sensing module 86 may continue to monitor the non-filtered signal output by A/D converter 112 to determine when noise is no longer detected. Since supplemental filter 122 may pose some risk of filtering out cardiac events, supplemental filter may only be activated when processor 80 determines that noise is present. In some examples, sensing module 86 may not include supplemental filter 122.

Figure 6:
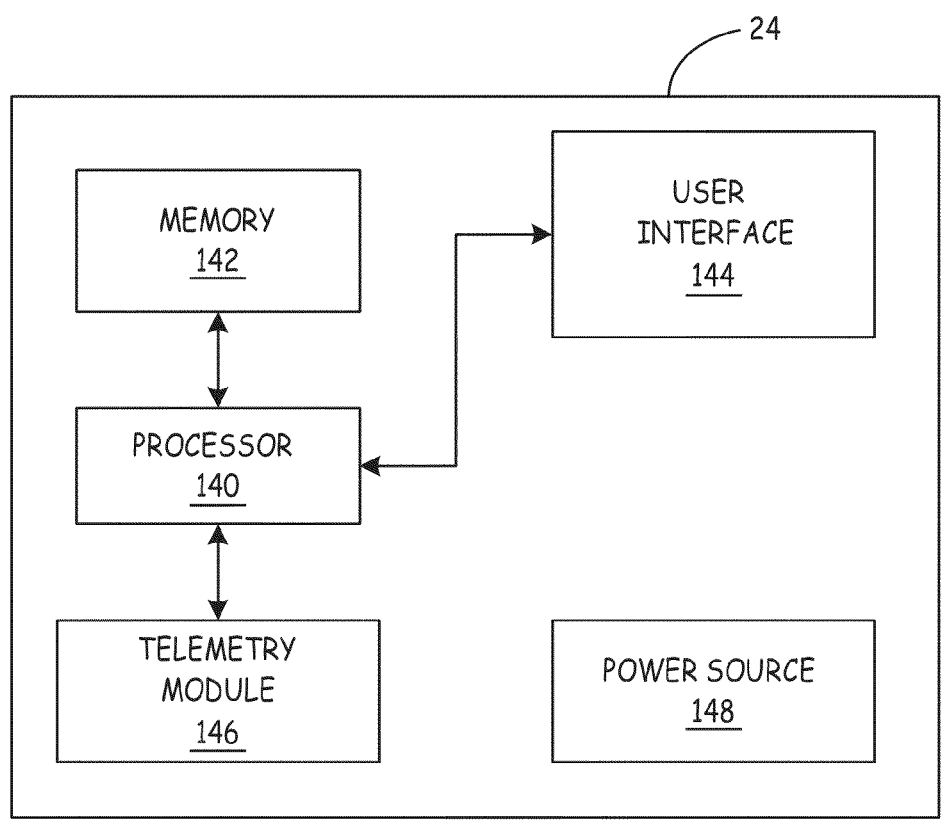
FIG. 6 is a functional block diagram illustrating an example configuration of an external programmer that facilitates user communication with the IMD.

FIG. 6 is functional block diagram illustrating an example configuration of programmer 24. As shown in FIG. 6, programmer 24 may include a processor 140, memory 142, user interface 144, telemetry module 146, and power source 148. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 144, which may include display to present graphical user interface to a user, and a keypad or another mechanism for receiving input from a user. In addition, the user may receive an alert from IMD 16 indicating a potential noise condition via programmer 24.

Processor 140 can take the form one or more microprocessors, DSPs, ASICs, FPGAs, programmable logic circuitry, or the like, and the functions attributed to processor 100 herein may be embodied as hardware, firmware, software or any combination thereof. Memory 142 may store instructions that cause processor 100 to provide the functionality ascribed to programmer 24 herein, and information used by processor 100 to provide the functionality ascribed to programmer 24 herein. Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 146, which may be coupled to an internal antenna or an external antenna. An external antenna that is coupled to programmer 24 may correspond to the programming head that may be placed over heart 12, as described above with reference to FIG. 1. Telemetry module 146 may be similar to telemetry module 88 of IMD 16 (FIG. 4).

Telemetry module 146 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 140 of programmer 24 and/or one or more processors of one or more networked computers may perform all or a portion of the techniques described herein with respect to processor 80 and IMD 16. For example, processor 140 or another processor may receive an EGM or other sensed signal for identification of noise.

Figure 7:
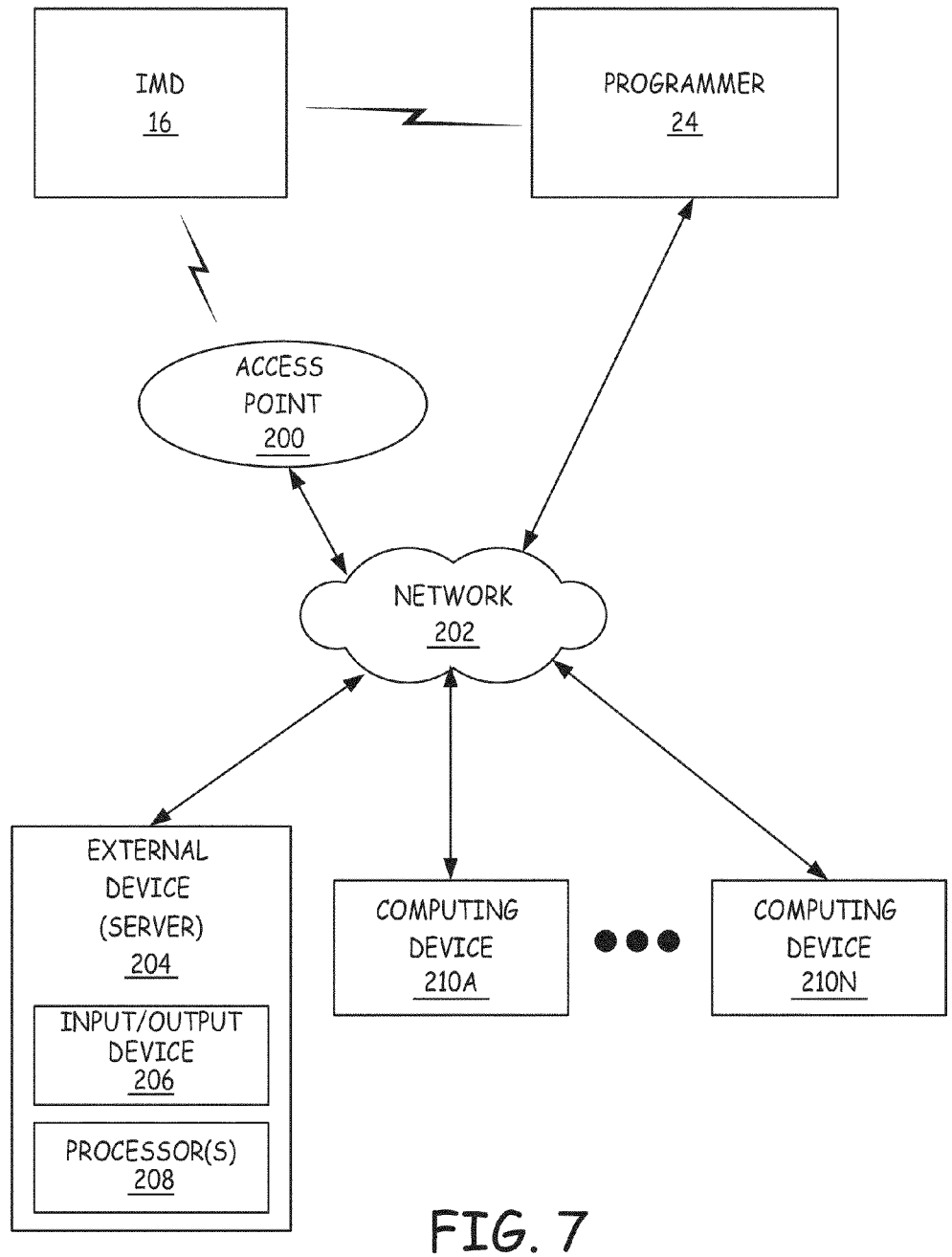
FIG. 7 is a block diagram illustrating an example system that includes an external device, such as a server, and one or more computing devices that are coupled to the IMD and programmer shown in FIG. 1 via a network.

FIG. 7 is a block diagram illustrating an example system that includes an external device, such as a server 204, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 6, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein.

Access point 200 may comprise a device that connects to network 202 via any of a variety of connections, such as telephone dial-up, digital subscriber line (DSL), or cable modem connections. In other examples, access point 200 may be coupled to network 202 through different forms of connections, including wired or wireless connections. In some examples, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16. In some examples, server 204 or computing devices 210 may control or perform any of the various functions or operations described herein, e.g., detect noise based on an analysis of a cardiac signal received from IMD 16 or control detection of noise by IMD 16.

In some cases, server 204 may be configured to provide a secure storage site for archival of sensing integrity information that has been collected from IMD 16 and/or programmer 24. Network 202 may comprise a local area network, wide area network, or global network, such as the Internet. In some cases, programmer 24 or server 204 may assemble sensing integrity information in web pages or other documents for viewing by and trained professionals, such as clinicians, via viewing terminals associated with computing devices 210. The system of FIG. 6 may be implemented, in some aspects, with general network technology and functionality similar to that provided by the Medtronic CareLink® Network developed by Medtronic, Inc., of Minneapolis, Minn.

Figure 8:
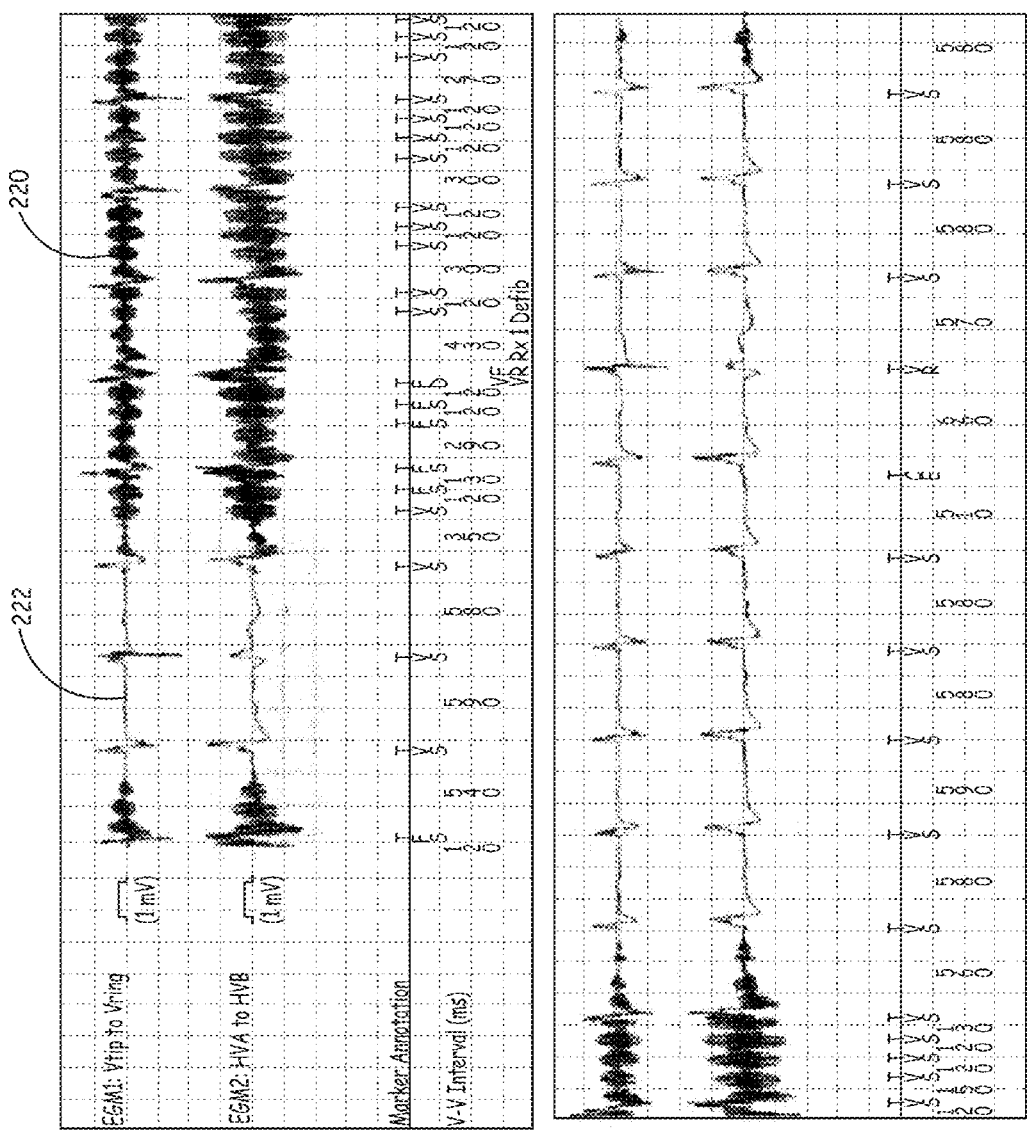
FIG. 8 illustrates an example electrogram (EGM) signal that includes electromagnetic interference (EMI).

FIG. 8 illustrates an example EGM signal that includes noise due to EMI. Noise 220 causes high frequency variations in EGM signal 222. Noise 220 may have a frequency of approximately 50 Hz or approximately 60 Hz, e.g., due to contact with ungrounded electrical appliances.

Figure 9:
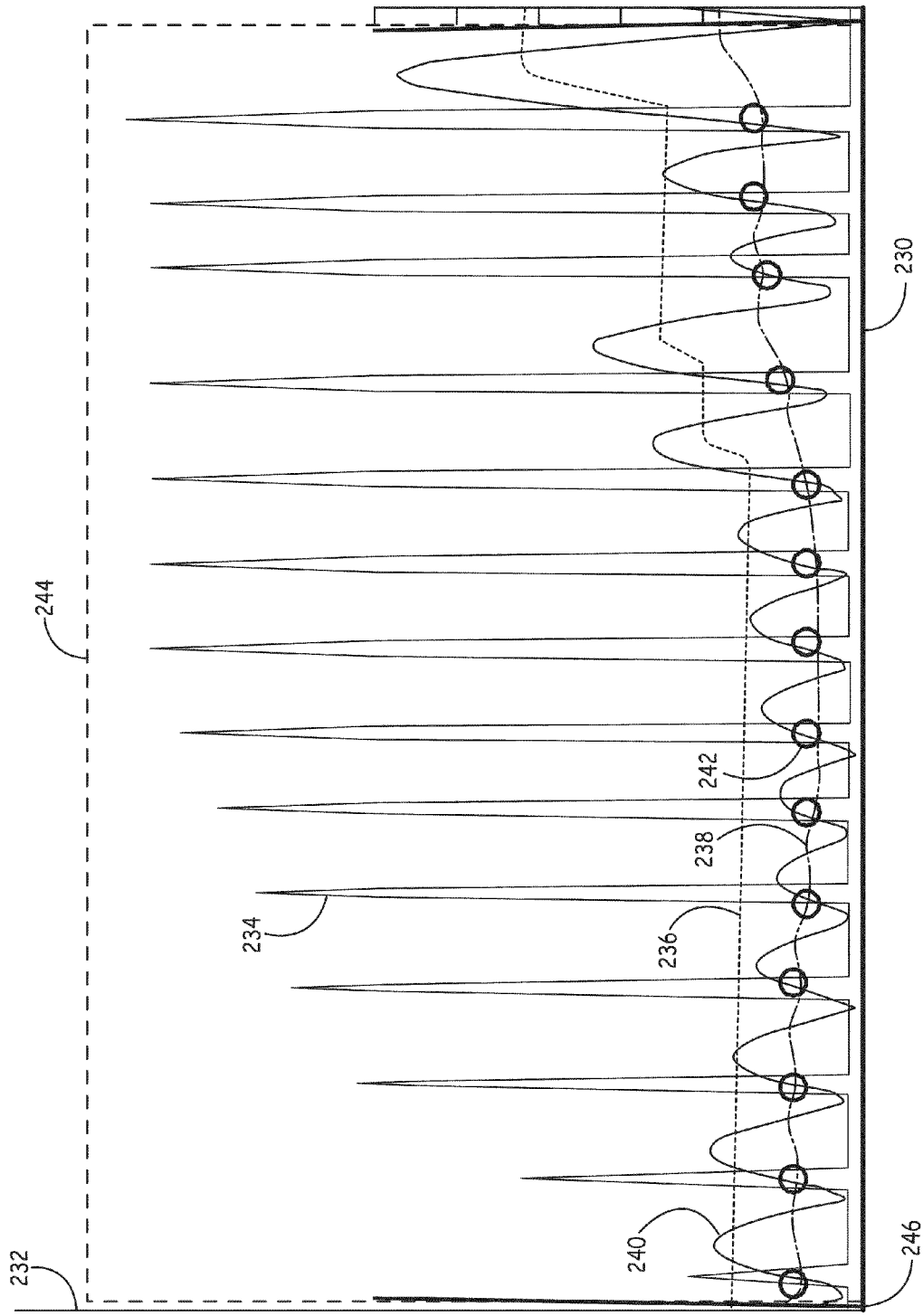
FIGS. 9-11 are timing diagrams illustrating example signal processing functions performed by the sensing module of FIG. 5.
Figure 10:
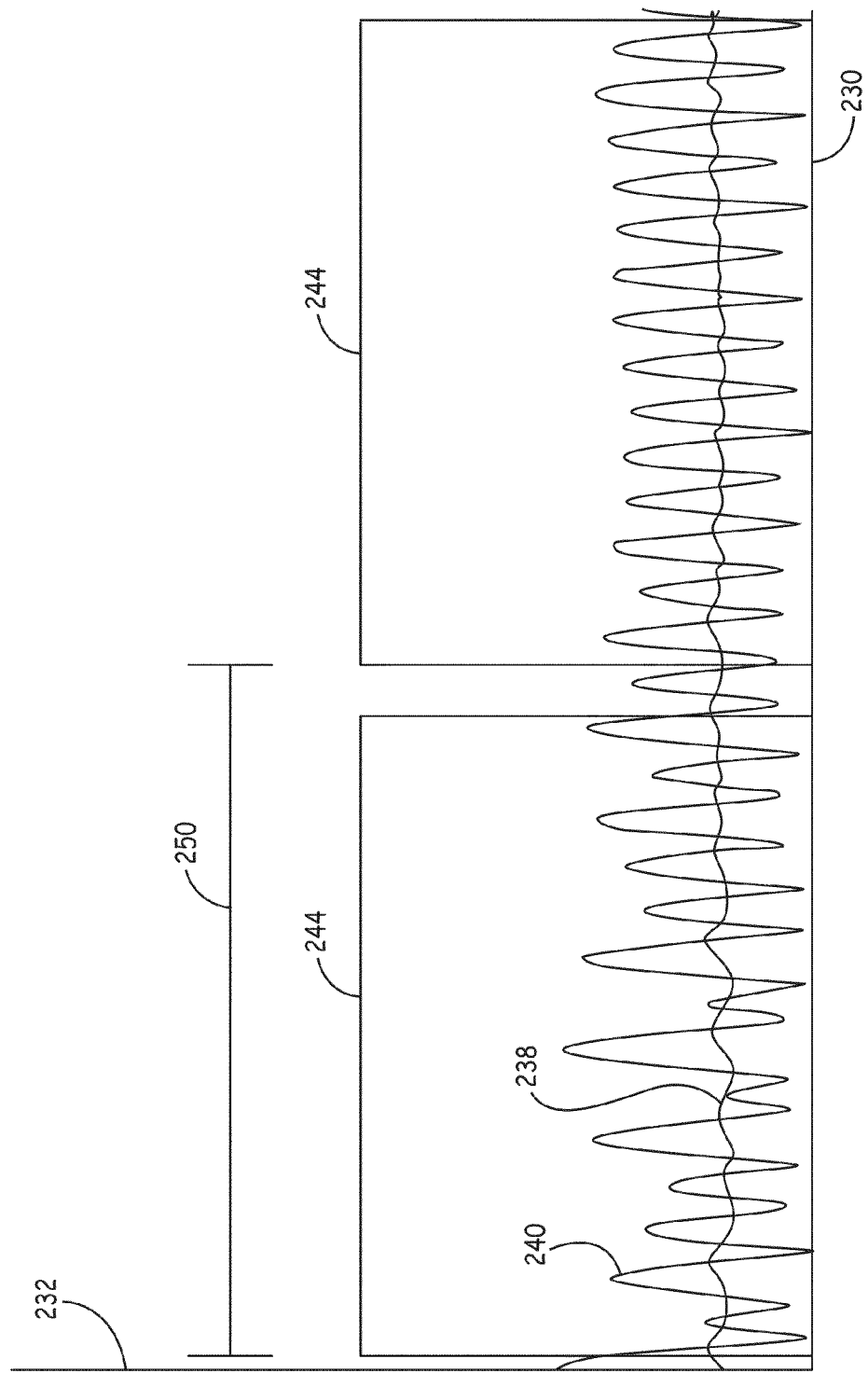
Figure 11:
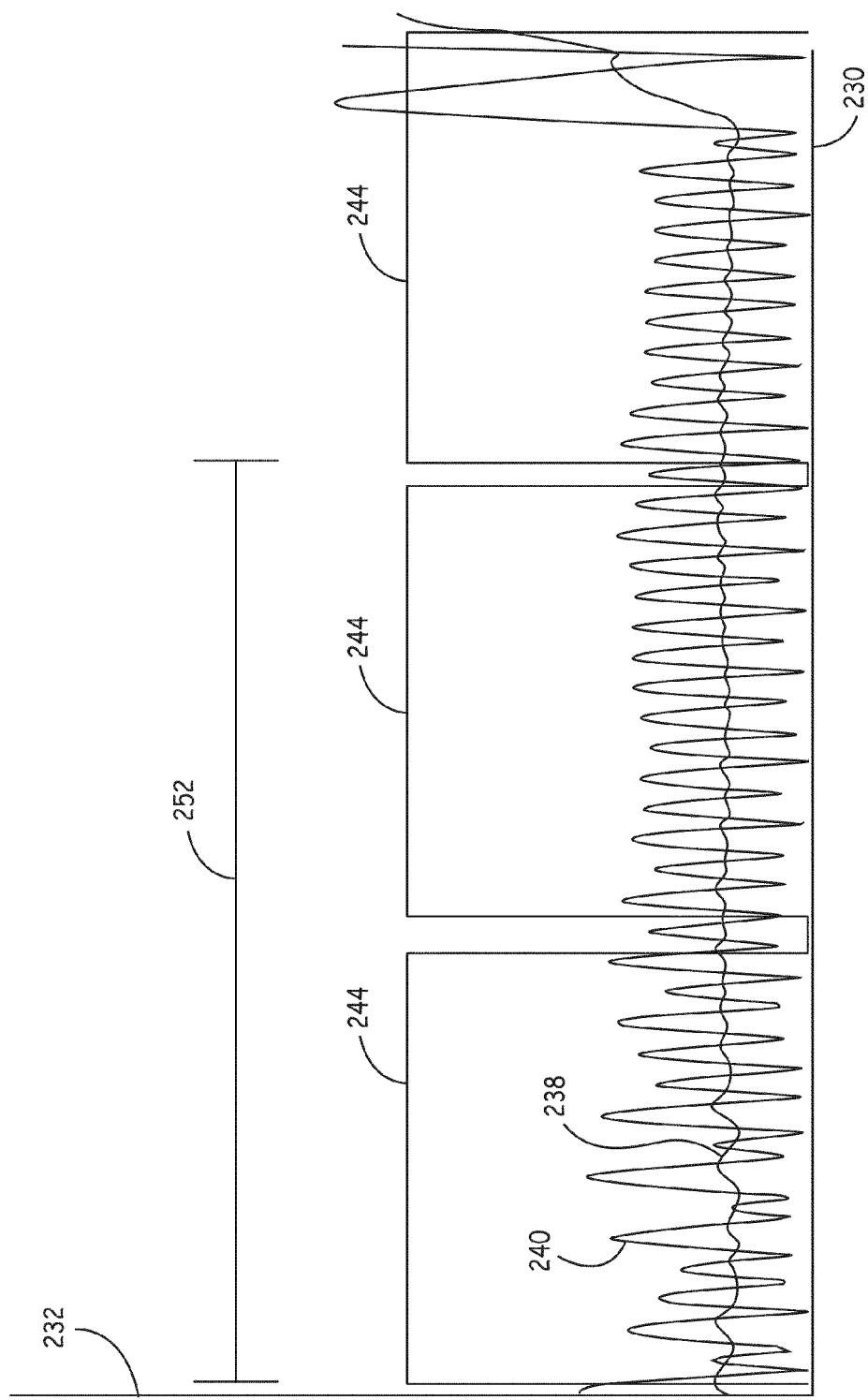

FIGS. 9-11 illustrate example signal processing functions performed by sensing module 86 (FIG. 5). Time is represented on horizontal axis 230, and amplitude is represented on vertical axis 232. EGM signal 234 is exhibiting fluctuations due to noise. EGM signal 234 is provided to A/D converter 112 and filter/rectifier 114 to produce filtered and rectified signal 240. Autothreshold signal 236 and threshold signal 238 are both determined based on filtered and rectified signal 240. Signal characteristic monitor 118 produces threshold signal 238 based on a characteristic of filtered and rectified signal 240. In the examples illustrated in FIGS. 9-11, threshold signal 238 equals one-half of a moving average of filtered and rectified signal 240. Threshold signal 238 may vary according to changes in the amplitude of filtered and rectified signal 240. In other examples, signal characteristic monitor 118 may produce a threshold signal based on low pass filtering of filtered and rectified signal 240.

Circles 242 illustrate where a rising edge of filtered and rectified signal 240 up crosses threshold signal 238. In the example illustrated in FIG. 9, this crossing point is used to count each peak, e.g., signal fluctuation, that exceeds threshold signal 238. In other examples, the point where a falling edge of filtered and rectified signal 240 down crosses threshold signal 238 may be counted instead. As another example, peaks of filtered and rectified signal 240 that exceed threshold signal 238 may be counted instead. Noise counter 120 may increment its count based on the number of signal fluctuations that meet the count criteria.

Sensing window 244 represents the sensing window for one heartbeat. Sensing window 224 may correspond to a blanking period subsequent to a detected cardiac event. For example, an R-wave or other cardiac event may be detected at time 246. Sensing window 244 may commence at time 246 corresponding to the detected cardiac event and run for a defined time period, e.g., of approximately 120 ms. Processor 80 (FIG. 4) may determine that noise is present if the count obtained by noise counter 120 during sensing window 244 exceeds a one heartbeat threshold value. In the example of FIG. 9, the count obtained by noise counter 120 during sensing window 244 is fourteen, and the one heartbeat threshold value is 10. Therefore, processor 80 determines that noise is present.

FIG. 10 illustrates filtered and rectified signal 240 and threshold signal 238 over two sensing windows 244 corresponding to two consecutive heartbeats. In some examples, processor 80 may determine that noise is present based on a cumulative noise count obtained over a plurality of heartbeats. For example, processor 80 may determine noise is present if the combined noise count over two sensing windows 244 exceeds a two heartbeat threshold. In some examples, processor 80 may also require the interval between heartbeats, e.g., R-R interval, to be less than a two heartbeat interval threshold, e.g., approximately 160 ms. In the example of FIG. 10, sensing windows 244 correspond to blanking periods that begin when R-waves are detected. Therefore, the R-R interval 250 corresponds to the time between the first sensing window 244 begins and the second sensing window 244 begins.

FIG. 11 illustrates filtered and rectified signal 240 and threshold signal 238 over three sensing windows 244 corresponding to three consecutive heartbeats. Processor 80 may determine noise is present if the combined noise count over three sensing windows 244 exceeds a three heartbeat threshold. In some examples, processor 80 may also require the interval between the first heartbeat and third heartbeat to be less than a three heartbeat interval threshold, e.g., approximately 380 ms. In the example of FIG. 11, sensing windows 244 correspond to blanking periods that begin when R-waves are detected. Therefore, the R-R interval from the first heartbeat to the third heartbeat 252 corresponds to the time between the first sensing window 244 begins and the third sensing window 244 begins. Monitoring a cumulative noise count over a plurality of heartbeats may allow processor 80 to detect intermittent noise or various other types of high frequency noise.

FIGS. 12-15 illustrate example EGMs in which the noise detection algorithm was applied. FIGS. 12-15 illustrate EGM signals 234, filtered and rectified signals 240, threshold signals 238, and sensing windows 244. If noise is detected for a sensing window, a marker 260 follows the sensing window.

Figure 12:
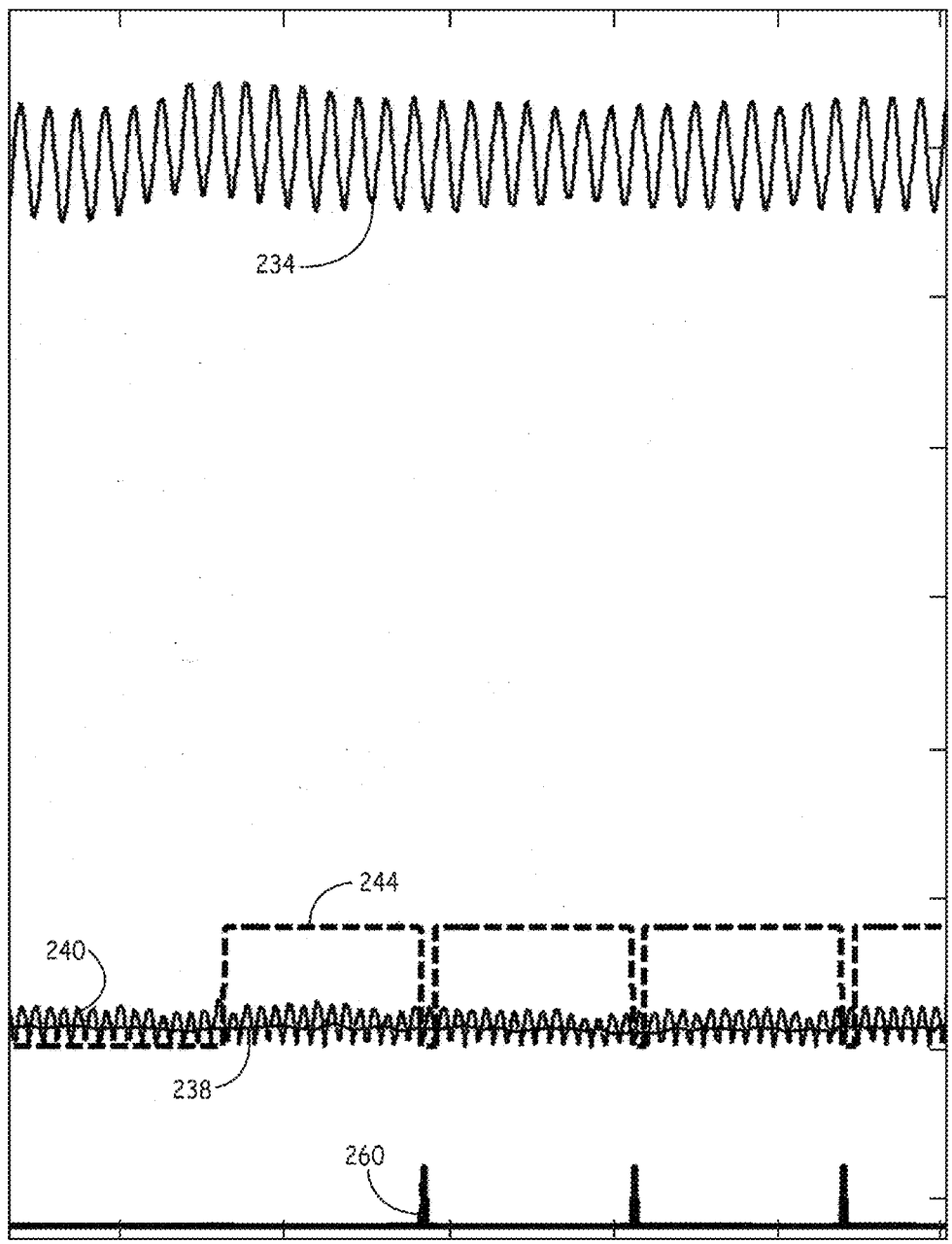
FIGS. 12-15 illustrate example EGMs in which the noise detection algorithm was applied.

In the example of FIG. 12, 60 Hz noise on EGM 234 is successfully detected, as indicated by markers 260 following each of sensing windows 244.

Figure 13:
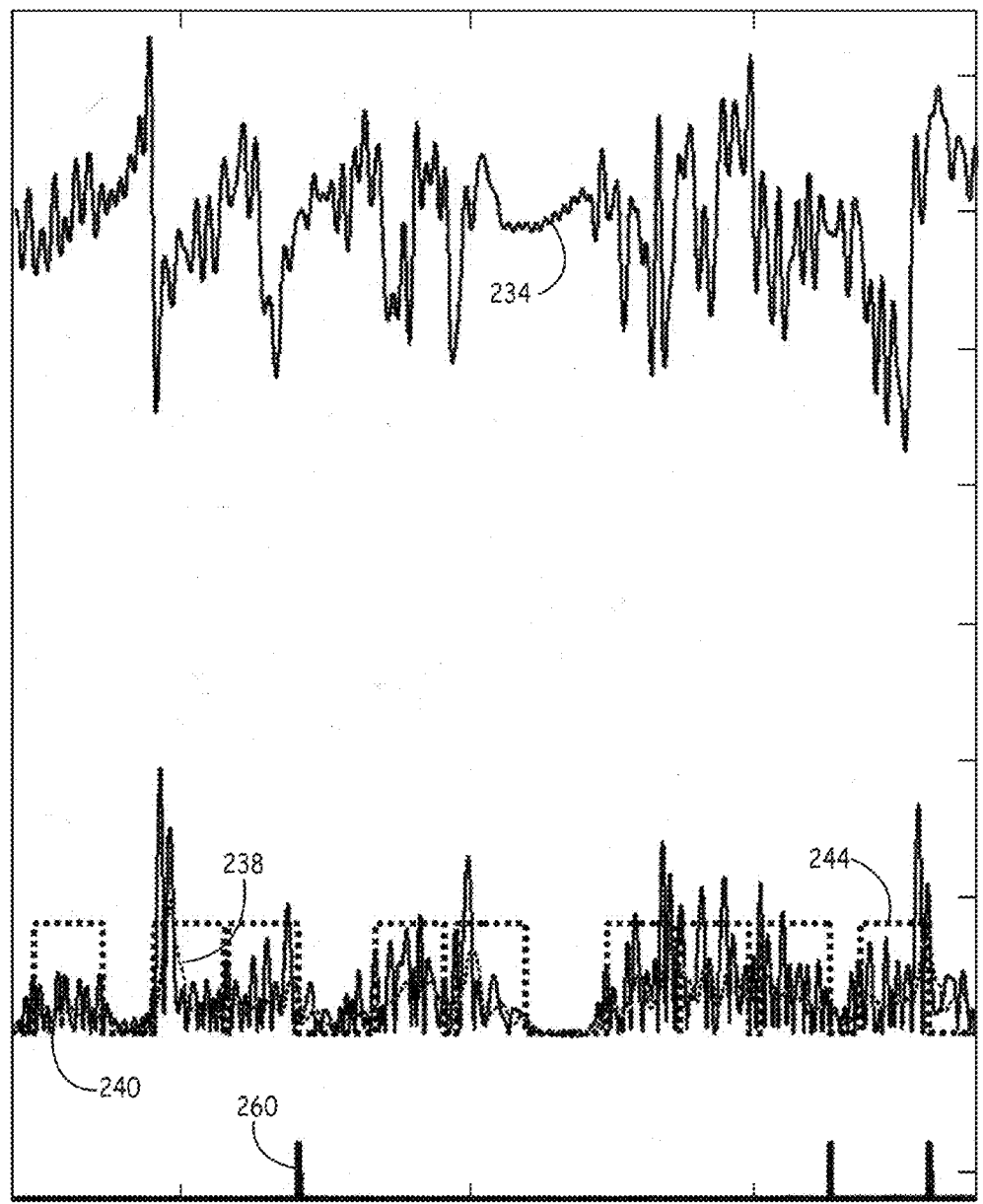

In the example of FIG. 13, another type of high frequency noise is detected for some sensing windows 244. The noise in the example of FIG. 13 is more intermittent than typical 50 or 60 Hz noise. Detecting noise based on a cumulative noise count over a plurality of consecutive heartbeats may be particularly effective in this example.

Figure 14:
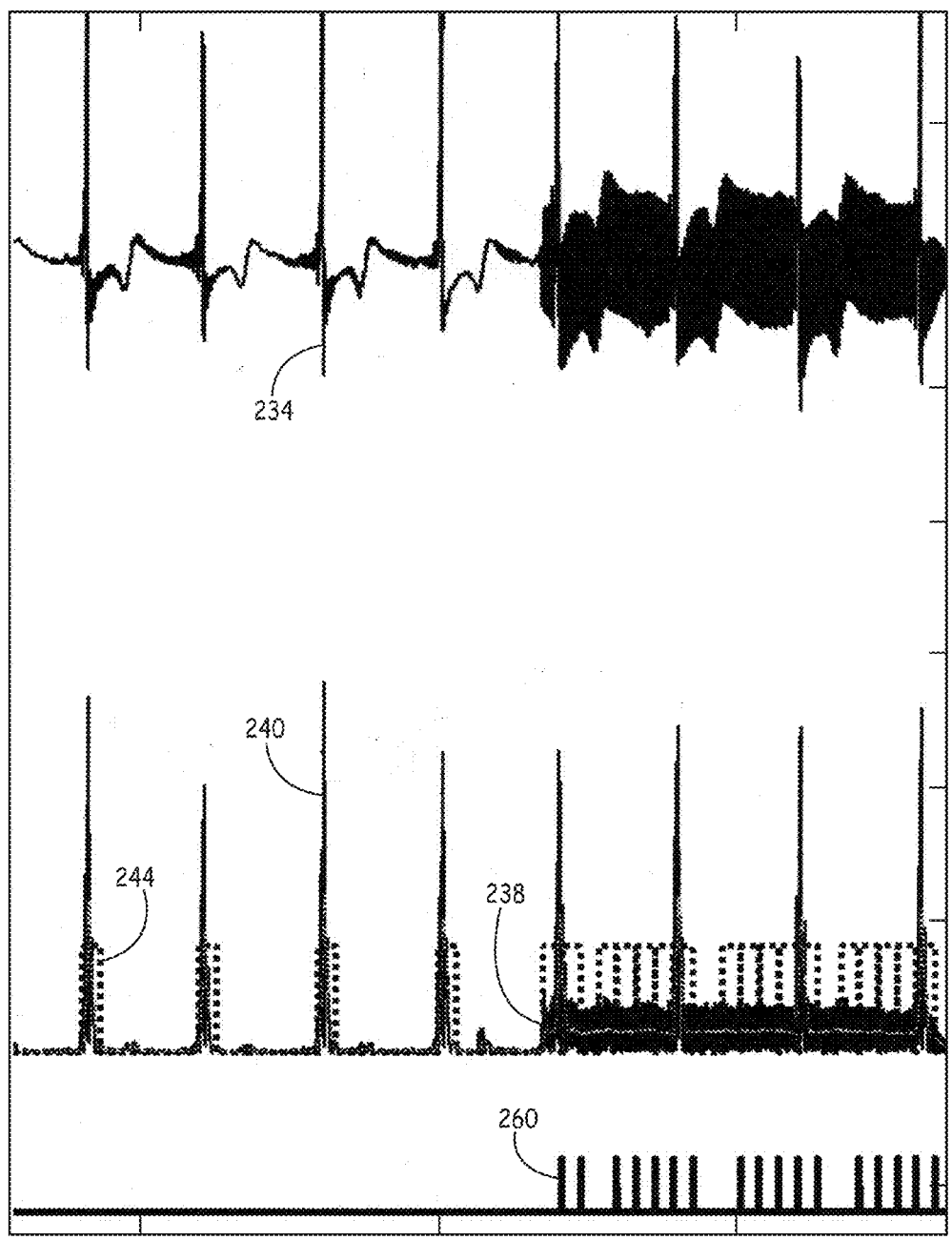

In the example of FIG. 14, intermittent noise due to EMI is appropriately detected.

Figure 15:
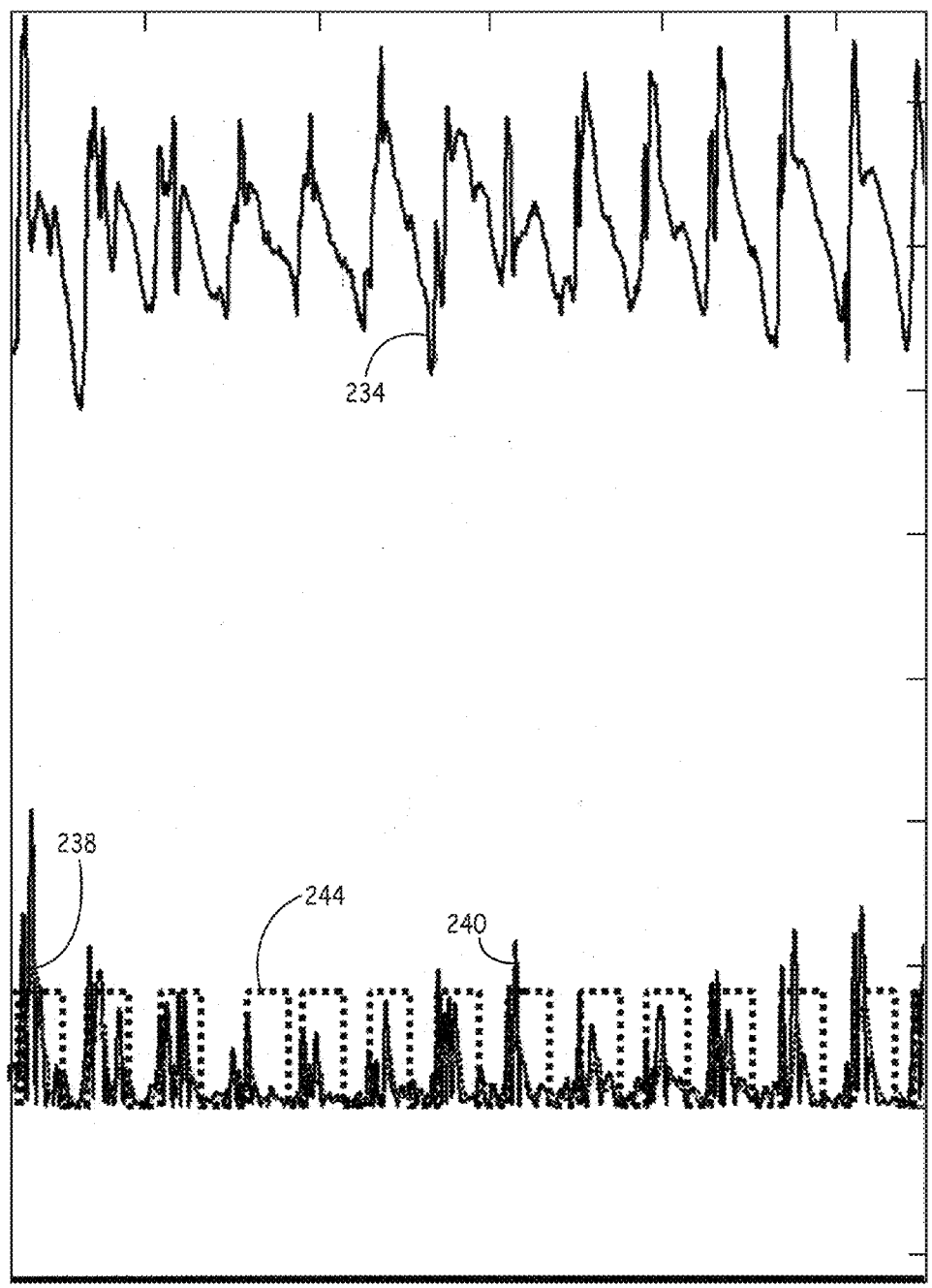

In the example of FIG. 15, EGM 234 indicates VF. The VF does not falsely trigger noise detection. Although VF may include high frequency components, the noise count for VF is not high enough to falsely trigger noise detection.

The noise detection algorithm was tested using developmental datasets. A first dataset included 13 EMI episodes gathered from 8 patients. The algorithm detected all 13 EMI episodes and did not falsely detect VF based on the EMI noise.

A second dataset included 35 EMI episodes gathered from 18 patients. The algorithm detected all 35 EMI episodes and did not falsely detect VF based on the EMI noise. Additionally, no EMI was falsely detected. The data set included 94 spontaneous VT/VF episodes; 150 induced episodes, e.g., VF, VT, normal sinus rhythm, sinus tachycardia, sampled at a frequency of 1 kilohertz; and 40 induced VF episodes sensed using right ventricular (RV) tip electrode to RV ring electrode and RV tip electrode to RV coil electrode configurations and sampled at a frequency of 1024 Hz.

The performance of the noise detection algorithm was also tested with 50 and 60 Hz notch filters. Most EMI episodes were rejected by the notch filters without compromising VF detection. For the first dataset, the algorithm detected all 13 EMI episodes gathered from 8 patients and did not falsely detect VF based on the EMI noise. For the second dataset, the algorithm detected all 35 EMI episodes and did not falsely detect VF based on the EMI noise. Six of the EMI episodes gathered from 3 patients were not rejected by the notch filter. No false detections is EMI episodes were found in the following data: 94 spontaneous VT/VF episodes; 150 induced episodes, e.g., VF, VT, normal sinus rhythm, sinus tachycardia, sampled at a frequency of 1 kilohertz; and 40 induced VF episodes sensed using right ventricular (RV) tip electrode to RV ring electrode and RV tip electrode to RV coil electrode configurations and sampled at a frequency of 1024 Hz. For 2 of the 150 induced episodes, the algorithm detected noise due to noisy recordings resulting from non-EMI noise.

Figure 16:
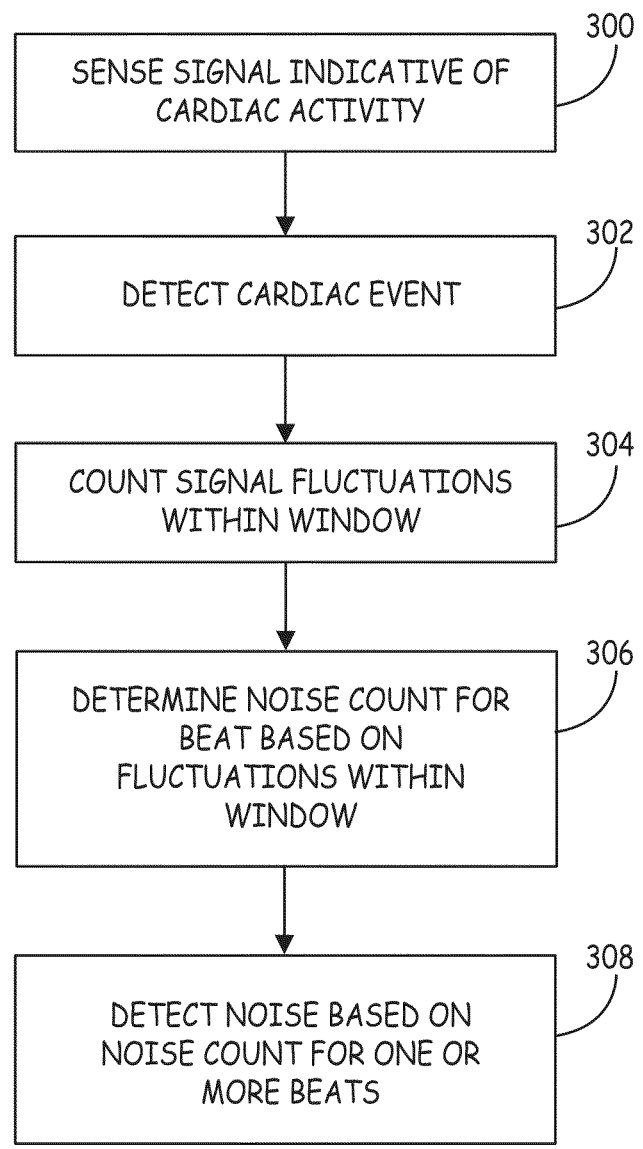
FIG. 16 is a flow diagram of an example method of detecting noise in a signal indicative of cardiac activity.

FIG. 16 is a flow diagram of an example method of detecting noise in a signal indicative of cardiac activity. Sensing module 86 receives a signal indicative of cardiac activity, such as an EGM, from one or more of electrodes 40, 42, 44, 46, 48, 50, 58, 62, 64 or 66 (300). Based on the sensed cardiac signal, sensing module 86 detects a cardiac event, e.g., depolarization (302). For example, sensing module 86 may utilize signal processing techniques to detect R-waves or other cardiac events based on the sensed cardiac signal.

Subsequent to detecting the cardiac event, sensing module 86 may count fluctuations of the cardiac signal within a sensing window (304). Sensing module 86 and, more particularly, signal characteristic monitor 118 of sensing module 86, may determine whether signal fluctuations meet defined criteria, e.g., exceed a threshold, and increment noise counter 120 of sensing module 86 based on the determination.

The sensing window may begin upon detection of the cardiac event, e.g., R-wave, and expire before the next cardiac event, e.g., the next R-wave. In some examples, the sensing window may correspond to a blanking period that follows a detected cardiac event. IMD 16 may withhold detection of cardiac events and therapy delivery during the blanking period. Therefore, noise detected during the blanking period may be due to sources other than therapy delivery. Furthermore, the sensing window, e.g., blanking period, may be sufficiently short such that signal fluctuations would not be physiologic, e.g., due to a subsequent normal or tachyarrhythmic cardiac depolarization, and instead would more likely be due to noise. Processor 80 may activate signal characteristic monitor 118 for a sensing window subsequent to each sensed cardiac event of a specified type, e.g., subsequent to each R-wave. As one example, the sensing window may be less than or equal to approximately 120 milliseconds (ms).

Processor 80 may receive the noise count 134 for the detected cardiac event from noise counter 120 upon expiration of a sensing window (306). Processor 80 may detect noise based on the noise count for one or more heartbeats (308). For example, processor 80 may compare the noise count 134 for the detected cardiac event, e.g., obtained during one sensing window associated with one heartbeat, to a one heartbeat threshold to determine whether noise is present. As described in further detail with respect to FIG. 18, in some examples, processor 80 may compare a cumulative count obtained over a plurality of consecutive sensing windows, e.g., over two or three sensing windows, to a corresponding threshold, e.g., to a two heartbeat or three heartbeat threshold, to determine whether noise is present.

Figure 17:
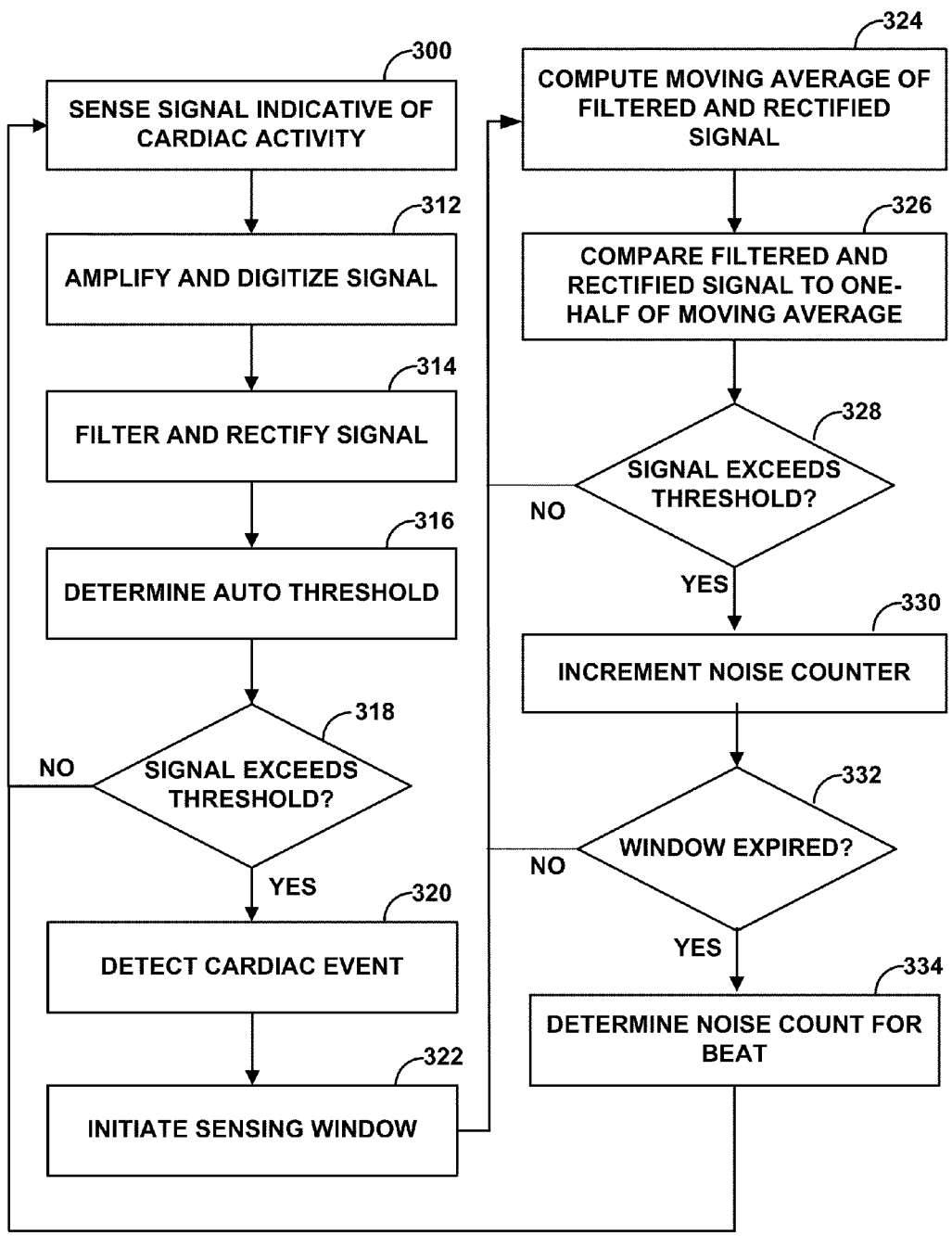
FIG. 17 is a flow diagram of an example method of determining noise counts within a sensing window to recognize noise in a signal indicative of cardiac activity.

FIG. 17 is a flow diagram of an example method of determining noise counts within a sensing window to recognize noise in a signal indicative of cardiac activity. A detection channel of sensing module 86 receives a signal indicative of cardiac activity, such as an EGM, from one or more of electrodes 40, 42, 44, 46, 48, 50, 58, 62, 64 or 66 (300). Amplifier 110 amplifies the sensed cardiac signal and A/D converter 112 converts the signal to a digital form (312). Filter/rectifier 114 filters and rectifies the digital signal (314). In some examples, filter/rectifier utilizes a bandpass filter, and the frequencies that filter/rectifier 114 passes may be based on the type of cardiac event, e.g., P- or R-wave, that sensing module 86 and, more particularly, the selected detection channel of sensing module 86, is configured to detect. As one example, filter/rectifier 114 may pass frequencies within the range of approximately 13 Hertz (Hz) to approximately 39 Hz when the selected detection channel of sensing module 86 is configured to detect R-waves.

Auto threshold module 116 may determine a threshold signal based on the filtered and rectified signal (316). The value of the threshold signal may automatically adjust based on the amplitude of the filtered and rectified signal. Auto threshold module 116 may provide an adjustable sensing threshold as a function of the measured P- or R-wave amplitude of the heart rhythm. Auto threshold module 116 may also compare values of the digital signal outputted by A/D converter 112 to values of the threshold signal (318). If a value of the digital signal outputted by A/D converter 112 does not exceed a corresponding threshold value, the detection channel of sensing module 86 may continue to monitor the signal indicative of cardiac activity (300). If a value of the digital signal outputted by A/D converter 112 exceeds a corresponding threshold value, auto threshold module 116 detect a cardiac event, such as a P-wave or R-wave, based on the comparison (320). Sensing module 86 may provide indications of detected cardiac events, such as P- and R-waves, to processor 80.

Upon detection of a cardiac event, processor 80 may initiate a sensing window to help facilitate noise recognition (322). The sensing window may run for a defined time period starting from the detection of the cardiac event. For example, the sensing window may be less than or equal to approximately 120 milliseconds. The sensing window may be sufficiently short such that signal fluctuations within the sensing window would not be physiologic, e.g., due to a subsequent normal or tachyarrhythmic cardiac depolarization, and instead would more likely be due to noise. The sensing window may expire before the next cardiac event, e.g. of the same type, is detected.

Signal characteristic monitor 118 may monitor a characteristic of the filtered and rectified signal output by filter/rectifier 114 during the sensing window to help facilitate noise recognition (324). Signal characteristic monitor 118 may also determine a threshold signal based on the monitored characteristic and compare the filtered and rectified signal to the threshold signal (326). In general, the signal characteristic of the filtered and rectified signal monitored by signal characteristic monitor 118 may provide an indication of the amplitude of the filtered and rectified signal, and signal characteristic monitor 118 may increment noise counter 120 based on fluctuations in the signal amplitude (330). Rapid signal fluctuations due to EMI or other noise may be interpreted by sensing module 86 as a plurality of sensed cardiac events, e.g., P- or R-waves, and result in inappropriate detection of a cardiac arrhythmia by IMD 16. More particularly, auto threshold module 116 of the selected sensing channel of sensing module 86 may interpret noise as cardiac events, e.g., P- or R-waves, and provide indications of the events to processor 80. The rate of sensed events when noise is present may be similar to or greater than that for detection of a tachyarrhythmia, and processor 80 may detect a tachyarrhythmia based on the noise.

In the example illustrated in FIG. 17, signal characteristic monitor 118 calculates a moving average of the filtered and rectified signal to help facilitate noise recognition (324). For example, signal characteristic monitor 118 may sample the filtered and rectified signal at approximately 1024 Hz and compute a moving average based on approximately 16 data points. Signal characteristic monitor 118 may also compare values of the filtered and rectified signal to values of a threshold signal that is based on the moving average (326). If a rising (or falling) edge of the filtered and rectified signal crosses a threshold value, e.g., approximately one half of the moving average (328), signal characteristic monitor 118 may increment noise counter 120 (330). In this manner, noise counter 120 may provide an indication of the number of signal fluctuations that may be attributed to noise, such as EMI. Signal characteristic monitor 118 may also require the value of the filtered and rectified signal to exceed a lower limit, such as one-fourth of a sensitivity setting, in order to increment noise counter 120. This may help prevent noise counter 120 from counting very low amplitude noise.

Signal characteristic monitor 118 may monitor a characteristic of the filtered and rectified signal to help facilitate noise recognition until a sensing window expires (332). For example, processor 80 may activate signal characteristic monitor 118 upon auto threshold module 116 detecting a specified type of cardiac event, e.g., a P- or R-wave (320). The sensing window may correspond to a blanking period. The blanking period may follow a detected cardiac event, e.g., a P- or R-wave. ICD 16 may withhold detection of cardiac events and therapy delivery during the blanking period. Therefore, noise detected during the blanking period may be due to sources other than therapy delivery. Processor 80 may activate signal characteristic monitor 118 for a sensing window subsequent to each sensed cardiac event of a specified type, e.g., subsequent to each R-wave. As one example, the sensing window may be less than or equal to approximately 120 milliseconds (ms).

Processor 80 may receive the noise count 134 for the detected cardiac event, e.g., obtained during one sensing window associated with one heartbeat, from noise counter 120 upon expiration of a sensing window (334). As described in further detail with respect to FIG. 18, processor may detect noise based on the noise count for one or more heartbeats.

Figure 18:
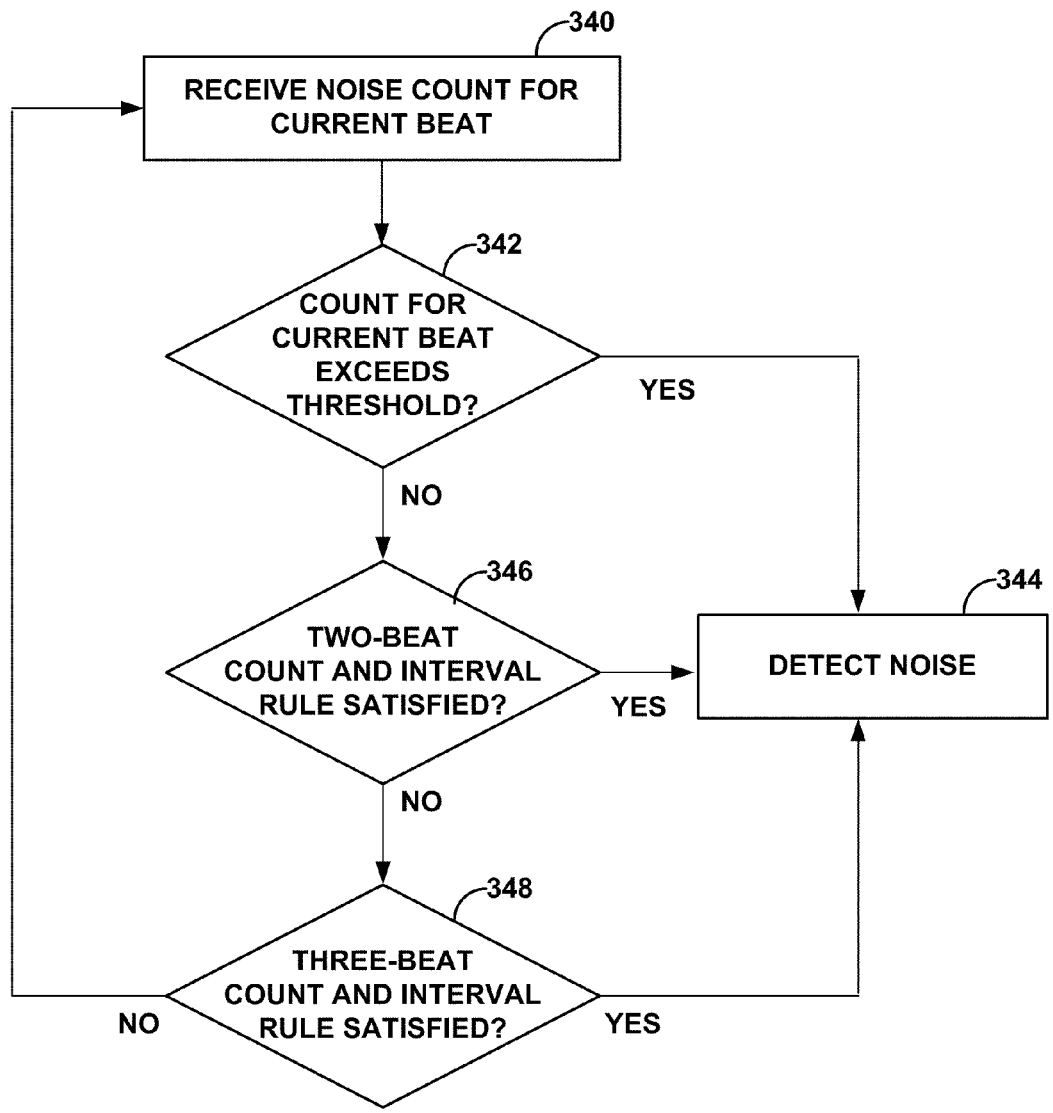
FIG. 18 is a flow diagram of an example method of detecting noise based on noise counts for one or more sensed cardiac beats.

FIG. 18 is a flow diagram of an example method of detecting noise based on noise counts for one or more sensed cardiac beats. Upon expiration of a sensing window for a current heartbeat, processor 80 may receive the noise count 134 for the detected cardiac event, e.g., obtained during one sensing window associated with the current heartbeat, from noise counter 120 (340). Processor 80 may determine whether the count for the current heartbeat exceeds a one-beat threshold (342). If the count exceeds the threshold, processor 80 may determine that noise, e.g., EMI, is present (344). As one example, processor 80 may determine noise is present if the count for the current heartbeat is greater than or equal to approximately 10 counts.

If the count for the current heartbeat does not exceed the one-beat threshold, processor 80 may determine whether a cumulative two heartbeat count for the current heartbeat and a preceding heartbeat meets two-beat criteria (346). For example, processor 80 may determine whether the cumulative count over the two consecutive heartbeats, e.g., R-waves, is greater than or equal to approximately 14 counts and the interval between the two consecutive heartbeats, e.g., R-R interval, is less than approximately 160 ms. If the two-beat criteria is met, processor 80 may determine that noise, e.g., EMI, is present (344).

If the two-beat criteria is not met, processor 80 may determine whether a cumulative three heartbeat count for the current heartbeat and two preceding heartbeats meets three-beat criteria (348). For example, processor 80 may determine whether the cumulative count over the three consecutive heartbeats, e.g., R-waves, is greater than or equal to approximately 19 counts and the interval from the first heartbeat to the third heartbeat is less than approximately 380 ms. If the three-beat criteria is met, processor 80 may determine that noise, e.g., EMI, is present (344).

The various noise count rules, e.g., for one, two, and three heartbeats, may account for various types of high frequency noise. The most common EMI signals on EGMs are at frequencies of approximately 50 Hz and approximately 60 Hz. The noise count gathered for one heartbeat may be sufficient to detect this type of noise. Processor 80 may detect intermittent noise or other types of noise by monitoring the noise count over a plurality of heartbeats. The count within noise counter 120 may be reset to zero upon expiration of a sensing window. Processor 80 may store, e.g., with memory 82, noise count values for previous heartbeats.

In general, tachyarrhythmias, e.g., VF, have high frequency signals, but the number of counts triggered for storage within noise counter 120 is less than the threshold set for noise detection. In this manner, sensing module 86 may detect high frequency noise, e.g., due to EMI, without falsely detecting noise due to tachyarrhythmias, such as VF.

FIG. 19 illustrates an EGM is which a notch filter is applied to attenuate 60 Hz noise. Signal 240A illustrates the filtered and rectified before the 60 Hz notch filter is applied. Signal 240B illustrates the filtered and rectified signal after the 60 Hz notch filter is applied. Additionally, in the example of FIG. 19, sensing windows 244 correspond to blanking periods and begin when cardiac depolarizations are detected. Sensing windows 244A indicate oversensing of cardiac events before the 60 Hz notch filter is applied. Sensing windows 244B indicate that oversensing is eliminated after the 60 Hz notch filter is applied.

Various examples of the invention have been described. These and other examples are within the scope of the following claims.

The invention claimed is:

1. A method comprising:
   sensing a signal indicative of cardiac activity;
   detecting a cardiac event based on the signal;
   determining a count of fluctuations of the signal within a window between the detected cardiac event and a next cardiac event; and
   determining whether noise is present in the signal based on the count,
   wherein determining the count of fluctuations of the signal comprises:
      monitoring a characteristic of the signal within the window between the detected cardiac event and the next cardiac event,
      determining a threshold signal based on the monitored characteristic of the signal,
      comparing values of the signal to values of the threshold signal, and
      incrementing a counter that indicates the count of fluctuations based on the comparison.

2. The method of claim 1, wherein the window begins upon detection of the cardiac event.

3. The method of claim 1, wherein the window comprises a blanking period in response to the detected cardiac event.

4. The method of claim 1, wherein the window is less than or equal to approximately 120 milliseconds.

5. The method of claim 1, wherein the characteristic of the signal comprises a moving average.

6. The method of claim 5, wherein the threshold signal comprises approximately one half of the moving average.

7. The method of claim 1, wherein the signal comprises a filtered and rectified signal.

8. The method of claim 1,
   further comprising detecting a plurality of cardiac events based on the cardiac signal,
   wherein determining a count of fluctuations of the signal within a window comprises determining a respective count of fluctuations of the signal within each of a plurality of windows, each of the windows between a respective pair of the cardiac events, and wherein determining whether noise is present comprises determining whether noise is present based on the plurality of counts.

9. The method of claim 8, wherein determining whether noise is present based on the plurality of counts comprises determining whether noise is present based on the plurality of counts and an interval between two of the plurality of detected events.

10. The method of claim 1, further comprising withholding at least one of tachyarrhythmia detection or tachyarrhythmia therapy in response to determining noise is present.

11. The method of claim 1, further comprising modifying a tachyarrhythmia detection count in response to determining noise is present.

12. The method of claim 1, further comprising applying a filter to the cardiac signal in response to determining noise is present.

13. The method of claim 1, further comprising providing an alert to a user subsequent to determining noise is present.

14. A system comprising:
a sensor that senses a signal indicative of cardiac activity;
a sensing module that detects a cardiac event based on the signal, wherein the sensing module is adapted to determine a count of fluctuations of the signal within a window between the detected cardiac event and a next cardiac event; and
a processor that determines whether noise is present in the signal based on the count,
wherein the sensing module:
monitors a characteristic of the signal within the window between the detected cardiac event and the next cardiac event;
determines a threshold signal based on the monitored characteristic of the signal;
compares values of the signal to values of the threshold signal; and
increments a counter indicating the count of fluctuations based on the comparison.

15. The system of claim 14, wherein the window begins upon the detection of the cardiac event by the sensing module.

16. The system of claim 14, wherein the window comprises a blanking period in response to the detected cardiac event.

17. The system of claim 14, wherein the window is less than or equal to approximately 120 milliseconds.

18. The system of claim 14, wherein the characteristic of the signal comprises a moving average.

19. The system of claim 14,
wherein the sensing module:
detects a plurality of cardiac events based on the cardiac signal; and
determines a respective count of fluctuations of the signal within each of a plurality of windows, each of the windows between a respective pair of the cardiac events, and
wherein the processor determines whether noise is present based on the plurality of counts.

20. The system of claim 19, wherein the processor determines whether noise is present based on the plurality of counts and an interval between two of the plurality of detected events.

21. The system of claim 14, wherein the sensor comprises a plurality of electrodes.

22. The system of claim 14, further comprising an implantable medical device that comprises the sensing module and at least one of comprises or is coupled to the sensor.

23. The system of claim 22, wherein the implantable medical device comprises the processor.

24. The system of claim 22, wherein the implantable medical device comprises at least one of a pacemaker, defibrillator, or cardioverter.

25. A system comprising:
means for sensing a signal indicative of cardiac activity;
means for detecting a cardiac event based on the signal;
means for determining a count of fluctuations of the signal within a window between the detected cardiac event and a next cardiac event; and
means for determining whether noise is present in the signal based on the count,
wherein the means for determining the count of fluctuations of the signal comprises:
means for monitoring a characteristic of the signal within the window between the detected cardiac event and the next cardiac event,
means for determining a threshold signal based on the monitored characteristic of the signal,
means for comparing values of the signal to values of the threshold signal, and
means for incrementing a counter that indicates the count of fluctuations based on the comparison.

26. A non-transitory computer readable medium comprising instructions, wherein the instructions cause a programmable processor to:
receive a signal indicative of cardiac activity;
detect a cardiac event based on the signal;
determine a count of fluctuations of the signal within a window between the detected cardiac event and a next cardiac event; and
determine whether noise is present in the signal based on the count,
wherein the instructions that cause the processor to determine the count of fluctuations of the signal comprise instructions that cause the processor to:
monitor a characteristic of the signal within the window between the detected cardiac event and the next cardiac event,
determine a threshold signal based on the monitored characteristic of the signal,
compare values of the signal to values of the threshold signal, and increment a counter that indicates the count of fluctuations based on the comparison.

* * * * *